(12) United States Patent
Kovarik et al.

(10) Patent No.: US 11,523,934 B2
(45) Date of Patent: *Dec. 13, 2022

(54) METHOD AND SYSTEM TO FACILITATE THE GROWTH OF DESIRED BACTERIA IN A HUMAN'S MOUTH

(71) Applicants: Joseph E. Kovarik, Englewood, CO (US); Katherine Rose Kovarik, Englewood, CO (US)

(72) Inventors: Joseph E. Kovarik, Englewood, CO (US); Katherine Rose Kovarik, Englewood, CO (US)

(73) Assignee: Seed Health, Inc., Venice, CA (US)

( * ) Notice: Subject to any disclaimer, the term of this patent is extended or adjusted under 35 U.S.C. 154(b) by 65 days.

This patent is subject to a terminal disclaimer.

(21) Appl. No.: 16/904,056

(22) Filed: Jun. 17, 2020

(65) Prior Publication Data
US 2020/0323679 A1 Oct. 15, 2020

Related U.S. Application Data

(63) Continuation-in-part of application No. 15/983,250, filed on May 18, 2018, now Pat. No. 10,687,975, which is a continuation-in-part of application No. 15/384,716, filed on Dec. 20, 2016, now Pat. No. 9,987,224, application No. 16/904,056, filed on Jun.
(Continued)

(51) Int. Cl.
*A61F 5/56* (2006.01)

(52) U.S. Cl.
CPC .................................. *A61F 5/566* (2013.01)

(58) Field of Classification Search
CPC .............................. A61K 9/006; A61F 5/566
See application file for complete search history.

(56) References Cited

U.S. PATENT DOCUMENTS 3,178,341 A   4/1965 Hamill et al.
3,832,460 A   8/1974 Kosti
(Continued)

FOREIGN PATENT DOCUMENTS

WO   WO 2009/052421   4/2009
WO   WO 2011/020780   2/2011
(Continued)

OTHER PUBLICATIONS

Hemert et al.: Migraine Associated with Gastrointestinal Disorders: Review of the Literature and Clinical Implications, Frontiers in Neurology, 2014, 5, 241.
(Continued)

*Primary Examiner* — Hong Yu
(74) *Attorney, Agent, or Firm* — Sheridan Ross P.C.

(57) ABSTRACT

A method to facilitate the growth of desired bacteria in a human's mouth by using a bioadhesive strip that has an encapsulated feature containing at least one bacteria that has one of a pathogenic or toxic element excised using a clustered regularly interspaced short palindromic repeats (CRISPR)-CRISPR associated protein (Cas) system or a CRISPR from *Prevotella* and *Francisella* 1 (Cpf1) system, and in particular, using oral strips that adhere to surfaces in the oral cavity and that include at least one of xylitol, *Lachnospira, Veillonella, Faecalibacterium* and/or *Rothia* bacteria.

20 Claims, 4 Drawing Sheets

Related U.S. Application Data 17, 2020, which is a continuation-in-part of application No. 14/752,192, filed on Jun. 26, 2015, now Pat. No. 9,549,842, which is a continuation-in-part of application No. 14/225,503, filed on Mar. 26, 2014, now Pat. No. 9,445,936, which is a continuation of application No. 13/367,052, filed on Feb. 6, 2012, now Pat. No. 8,701,671, application No. 16/904,056, filed on Jun. 17, 2020, which is a continuation-in-part of application No. 15/270,034, filed on Sep. 20, 2016, now Pat. No. 9,750,802, which is a continuation-in-part of application No. 14/954,074, filed on Nov. 30, 2015, now Pat. No. 9,457,077, which is a continuation-in-part of application No. 14/574,517, filed on Dec. 18, 2014, now Pat. No. 9,408,880, application No. 16/904,056, filed on Jun. 17, 2020, which is a continuation-in-part of application No. 15/228,454, filed on Aug. 4, 2016, now Pat. No. 9,585,920, application No. 16/904,056, filed on Jun. 17, 2020, which is a continuation-in-part of application No. 14/611,458, filed on Feb. 2, 2015, now Pat. No. 10,398,209, which is a continuation of application No. 14/502,097, filed on Sep. 30, 2014, now Pat. No. 9,010,340, which is a continuation of application No. 14/307,651, filed on Jun. 18, 2014, now Pat. No. 8,936,030, which is a continuation-in-part of application No. 14/079,054, filed on Nov. 13, 2013, now Pat. No. 8,757,173, which is a continuation of application No. 13/425,913, filed on Mar. 21, 2012, now Pat. No. 8,584,685.

(60) Provisional application No. 62/387,405, filed on Dec. 24, 2015, provisional application No. 61/439,652, filed on Feb. 4, 2011, provisional application No. 61/566,023, filed on Nov. 4, 2011, provisional application No. 62/072,476, filed on Oct. 30, 2014, provisional application No. 62/053,926, filed on Sep. 23, 2014, provisional application No. 62/014,855, filed on Jun. 20, 2014, provisional application No. 61/919,297, filed on Dec. 20, 2013, provisional application No. 62/387,404, filed on Dec. 24, 2015, provisional application No. 62/274,550, filed on Jan. 4, 2016, provisional application No. 62/275,341, filed on Jan. 6, 2016, provisional application No. 61/467,767, filed on Mar. 25, 2011.

(56) References Cited

U.S. PATENT DOCUMENTS

| | | | |
|---|---|---|---|
| 4,136,162 | A | 1/1979 | Fuchs et al. |
| 4,568,639 | A | 2/1986 | Lew |
| 4,687,841 | A | 8/1987 | Spilburg et al. |
| 4,720,486 | A | 1/1988 | Spilburg et al. |
| 4,995,555 | A | 2/1991 | Woodruff |
| 5,002,970 | A | 3/1991 | Eby, III |
| 5,277,877 | A | 1/1994 | Jeffrey et al. |
| 5,614,501 | A | 3/1997 | Richards |
| 5,719,196 | A | 2/1998 | Uhari |
| 6,054,143 | A | 4/2000 | Jones |
| 6,139,861 | A | 10/2000 | Friedman |
| 6,210,699 | B1 | 4/2001 | Acharya |
| 6,287,610 | B1 | 9/2001 | Bowling et al. |
| 6,569,474 | B2 | 5/2003 | Clayton et al. |
| 6,599,883 | B1 | 7/2003 | Romeo |
| 6,722,577 | B2 | 4/2004 | Dobyns, III |
| 6,919,373 | B1 | 7/2005 | Lam et al. |
| 7,087,249 | B2 | 8/2006 | Burrelll |
| 7,267,975 | B2 | 9/2007 | Strobel et al. |
| 7,353,194 | B1 | 4/2008 | Kerker et al. |
| 7,540,432 | B2 | 6/2009 | Majerowski et al. |
| 7,650,848 | B2 | 1/2010 | Brennan |
| 7,820,420 | B2 | 10/2010 | Whitlock |
| 7,862,808 | B2 | 1/2011 | Isolauri et al. |
| 7,901,925 | B2 | 3/2011 | Bojrab |
| 8,034,606 | B2 | 10/2011 | Park et al. |
| 8,197,872 | B2 | 6/2012 | Mills et al. |
| 8,349,313 | B2 | 1/2013 | Smith et al. |
| 8,420,074 | B2 | 4/2013 | Rehberger et al. |
| 8,454,729 | B2 | 6/2013 | Mittelmark et al. |
| 8,481,299 | B2 | 7/2013 | Gueniche |
| 8,496,914 | B2 | 7/2013 | Bonfiglio |
| 8,585,588 | B2 | 11/2013 | Kovarik et al. |
| 8,685,389 | B2 | 4/2014 | Baur |
| 8,701,671 | B2 | 4/2014 | Kovarik |
| 8,716,327 | B2 | 5/2014 | Zhao |
| 8,758,764 | B2 | 6/2014 | Masignani et al. |
| 8,815,538 | B2 | 8/2014 | Lanzalaco et al. |
| 8,865,211 | B2 | 10/2014 | Tzannis |
| 8,951,775 | B2 | 2/2015 | Castiel |
| 8,999,372 | B2 | 4/2015 | Davidson |
| 9,011,834 | B1 | 4/2015 | McKenzie et al. |
| 9,017,718 | B2 | 4/2015 | Tan |
| 9,028,841 | B2 | 5/2015 | Henn et al. |
| 9,131,884 | B2 | 9/2015 | Holmes |
| 9,234,204 | B2 | 1/2016 | Qvit-Raz et al. |
| 9,288,981 | B2 | 3/2016 | Gandhi et al. |
| 9,987,224 | B2 * | 6/2018 | Kovarik ............... A61K 35/74 |
| 10,687,975 | B2 | 6/2020 | Kovarik et al. |
| 2003/0031737 | A1 | 2/2003 | Rosenbloom |
| 2003/0206995 | A1 | 11/2003 | Bowling et al. |
| 2004/0053352 | A1 | 3/2004 | Ouyang et al. |
| 2004/0057962 | A1 * | 3/2004 | Timmerman ......... A61K 39/12 |
| | | | 424/190.1 |
| 2004/0096569 | A1 | 5/2004 | Barkalow et al. |
| 2004/0115223 | A1 | 6/2004 | Follansbee |
| 2004/0120991 | A1 | 6/2004 | Schobel |
| 2004/0142463 | A1 | 7/2004 | Walker et al. |
| 2004/0166501 | A1 | 8/2004 | Azimzai et al. |
| 2004/0228804 | A1 | 11/2004 | Jones et al. |
| 2005/0118655 | A1 | 6/2005 | Weinstock et al. |
| 2005/0196358 | A1 | 9/2005 | Georglades et al. |
| 2006/0035008 | A1 | 2/2006 | Virgalli et al. |
| 2006/0252087 | A1 | 11/2006 | Tang et al. |
| 2007/0054008 | A1 | 3/2007 | Clayton et al. |
| 2007/0057086 | A1 | 3/2007 | Van Kippersluis |
| 2007/0059718 | A1 | 3/2007 | Toner et al. |
| 2007/0059774 | A1 | 3/2007 | Grisham et al. |
| 2007/0063026 | A1 | 3/2007 | Mamaropolos et al. |
| 2007/0087020 | A1 | 4/2007 | O'Connor |
| 2007/0093420 | A1 | 4/2007 | Yeomans |
| 2007/0207955 | A1 | 9/2007 | Tanihara et al. |
| 2007/0218114 | A1 | 9/2007 | Sorousch |
| 2007/0231923 | A1 | 10/2007 | Cumberland et al. |
| 2008/0112983 | A1 | 5/2008 | Bufe et al. |
| 2008/0267933 | A1 | 10/2008 | Ohlson et al. |
| 2008/0286210 | A1 | 11/2008 | He |
| 2008/0305089 | A1 | 12/2008 | Bufe et al. |
| 2009/0004275 | A1 * | 1/2009 | Martyn ................. A61K 38/28 |
| | | | 514/1.1 |
| 2009/0130199 | A1 | 5/2009 | Kovacs |
| 2009/0196907 | A1 | 8/2009 | Bunick |
| 2009/0196908 | A1 | 8/2009 | Lee |
| 2009/0205083 | A1 | 8/2009 | Gupta et al. |
| 2010/0029832 | A1 | 2/2010 | Pinnavaia et al. |
| 2010/0260720 | A1 | 10/2010 | Sprenger |
| 2010/0285098 | A1 | 11/2010 | Haley |
| 2011/0142942 | A1 | 6/2011 | Gardner et al. |
| 2011/0217368 | A1 | 9/2011 | Prakash et al. |
| 2012/0027786 | A1 | 2/2012 | Gupta |
| 2012/0029832 | A1 | 2/2012 | Dodgson |
| 2012/0039806 | A1 | 2/2012 | Lahoud et al. |
| 2012/0058094 | A1 | 3/2012 | Blasser et al. |
| 2012/0128597 | A1 | 5/2012 | Peters et al. |
| 2012/0142548 | A1 | 6/2012 | Corsi et al. |
| 2012/0222685 | A1 | 9/2012 | Kovarik |
| 2012/0276143 | A1 | 11/2012 | O'Mahony et al. |
| 2012/0276525 | A1 | 11/2012 | Kovarik et al. |

(56) References Cited

U.S. PATENT DOCUMENTS

| | | |
|---|---|---|
| 2013/0059815 A1 | 3/2013 | Fournell et al. |
| 2013/0157876 A1 | 6/2013 | Lynch et al. |
| 2013/0259834 A1 | 10/2013 | Klaenhammer |
| 2013/0315869 A1 | 11/2013 | Qimron et al. |
| 2013/0323025 A1 | 12/2013 | Crawford et al. |
| 2013/0323100 A1 | 12/2013 | Poulton et al. |
| 2013/0330215 A1 | 12/2013 | Li |
| 2014/0044677 A1 | 2/2014 | Qvit-Raz et al. |
| 2014/0045744 A1 | 2/2014 | Gordon |
| 2014/0065209 A1 | 3/2014 | Putaala et al. |
| 2014/0065218 A1 | 3/2014 | Lang et al. |
| 2014/0066817 A1 | 3/2014 | Kovarik et al. |
| 2014/0068797 A1 | 3/2014 | Doudna et al. |
| 2014/0154290 A1 | 6/2014 | Peters et al. |
| 2014/0199266 A1 | 7/2014 | Park |
| 2014/0238411 A1 | 8/2014 | Kovarik |
| 2014/0255351 A1 | 9/2014 | Berstad et al. |
| 2014/0271867 A1 | 9/2014 | Myers |
| 2014/0333003 A1 | 11/2014 | Allen |
| 2014/0349405 A1 | 11/2014 | Sontheimer et al. |
| 2014/0356460 A1 | 12/2014 | Lutin |
| 2014/0363441 A1 | 12/2014 | Grandea, III et al. |
| 2014/0377278 A1 | 12/2014 | Elinav et al. |
| 2015/0017227 A1 | 1/2015 | Kim |
| 2015/0045546 A1 | 2/2015 | Siksnys et al. |
| 2015/0064138 A1 | 3/2015 | Lu et al. |
| 2015/0071957 A1 | 3/2015 | Kelly |
| 2015/0086581 A1 | 3/2015 | Li et al. |
| 2015/0093473 A1 | 4/2015 | Barrangou |
| 2015/0132263 A1 | 5/2015 | Liu et al. |
| 2015/0150792 A1 | 6/2015 | Klingman |
| 2015/0166641 A1 | 6/2015 | Goodman |
| 2015/0190435 A1 | 7/2015 | Henn et al. |
| 2015/0216917 A1 | 8/2015 | Jones |
| 2015/0252358 A1 | 9/2015 | Maeder |
| 2015/0329555 A1 | 11/2015 | Liras |
| 2015/0329875 A1 | 11/2015 | Gregory |
| 2015/0352023 A1 | 12/2015 | Berg |
| 2015/0353901 A1 | 12/2015 | Liu |
| 2015/0361436 A1 | 12/2015 | Hitchcock |
| 2015/0374607 A1 | 12/2015 | Lanzalaco et al. |
| 2016/0008412 A1 | 1/2016 | Putaala et al. |
| 2016/0040216 A1 | 2/2016 | Wilder |
| 2016/0089315 A1 | 3/2016 | Kleinberg et al. |
| 2016/0089405 A1 | 3/2016 | Lue |
| 2016/0151427 A1 | 6/2016 | Whitlock et al. |
| 2016/0168594 A1 | 6/2016 | Zhang et al. |
| 2016/0206564 A1 | 7/2016 | Trachtman |
| 2016/0271189 A1 | 9/2016 | Cutcliffe |
| 2016/0314281 A1 | 10/2016 | Apte |

FOREIGN PATENT DOCUMENTS

| | | |
|---|---|---|
| WO | WO 2011/029701 | 5/2013 |
| WO | WO 2013/107750 | 7/2013 |
| WO | WO 2013/182038 | 12/2013 |

OTHER PUBLICATIONS

Mach et al.: Endurance exercise and gut microbiota: A review, Journal of Sport and Health Science, vol. 6, Issue 2, Jun. 2017, pp. 179-197.

Sivieri et al. (Lactobacillus acidophilus CRL 1014 improved "gut health" in the Shime reactor, BMC Gastroenterology, 201313:10.

Fiber-Famished Gut Microbes Linked to Poor Health: retrieved from internet: https://www.scientificamerican.com/article/fiber-famished-gut-microbes-linked-to-poor-health1/. Retrieved on Oct. 26, 2017.

Klingspor et al.: Enterococcus faecium NCIMB Modulates Epithelial Integrity, Heat Shock Protein, and Proinflammatory Cytokine Response in Intestinal Cells, Mediators of Inflammation, vol. 2015 (2015), Article ID 304149, 11 pages.

Spinler et al.: Human-derived probiotic Lactobacillus reuteri demonstrate antimicrobial activities targeting diverse enteric bacterial pathogens, Anaerobe, vol. 14, Issue 3, Jun. 2008, pp. 166-171.

Basseri et al.: Antibiotics for the Treatment of Irritable Bowel Syndrome, Gastroenterology Hepatology (NY). Jul. 2011; 7(7): 455-493.

McFadzean: Exercise can help modulate human gut microbiota, retrieved from internet: https://scholar.colorado.edu/cgi/viewcontent.cgilarticle=1154& context=honr_theses. Retived on May 20, 2019.

Chen et al.: Targeting Aldehyde Dehydrogenase 2: New Therapeutic Opportunities, retrieved frominternet: https://www.ncbi.nlm.nih.gov/pmc/articles/PMC3929114/?report=printable. retrieved on Feb. 28, 2019.

The structure behind the simplicity of CRISPR/Cas9: retrieved from internet: https://thescinder.com/2015/12/23the-structure-behind-the-simplicity-of-crisprcas9/. Retrieved Feb. 28, 2019.

* cited by examiner

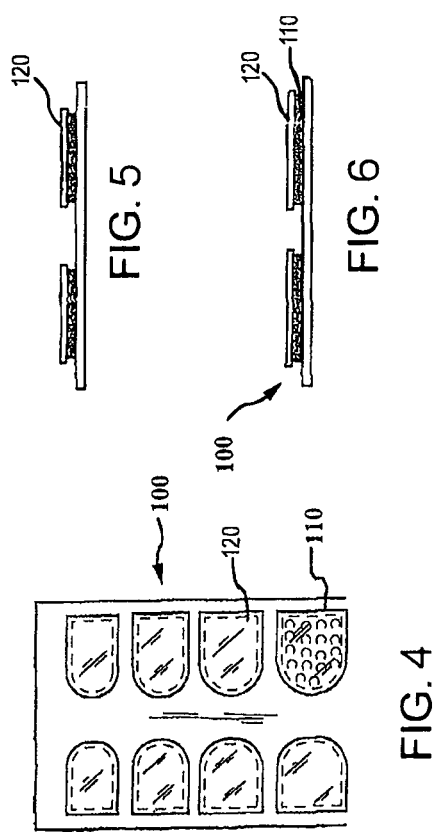

METHOD AND SYSTEM TO FACILITATE THE GROWTH OF DESIRED BACTERIA IN A HUMAN'S MOUTH

RELATED APPLICATIONS

This application is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Ser. No. 62/387,405, filed on Dec. 24, 2015.

This application is a continuation-in-part application of U.S. patent application Ser. No. 14/752,192 filed Jun. 26, 2015 (now U.S. Pat. No. 9,549,842, issued Jan. 24, 2017), which is a continuation-in-part application of U.S. patent application Ser. No. 14/225,503 filed Mar. 26, 2014, (now issued U.S. Pat. No. 9,445,936, issued Sep. 20, 2016), which is a continuation of U.S. patent application Ser. No. 13/367,052, filed Feb. 6, 2012 (now issued U.S. Pat. No. 8,701,671, issuing on Apr. 22, 2014), which claims priority of U.S. Provisional Patent Application Ser. No. 61/439,652, filed on Feb. 4, 2011 and U.S. Provisional Patent Application Ser. No. 61/556,023, filed on Nov. 4, 2011.

This application also is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016), which is a continuation-in-part application of U.S. patent application Ser. No. 14/574,517, filed on Dec. 18, 2014 (now issued U.S. Pat. No. 9,408,880, issuing on Aug. 9, 2016), which claims priority of U.S. Provisional Patent Application Ser. Nos. 62/072,476, filed on Oct. 30, 2014; 62/053,926, filed on Sep. 23, 2014; 62/014,855, filed on Jun. 20, 2014; and 61/919,297, filed on Dec. 20, 2013.

This application is also a continuation-in-part application of U.S. patent application Ser. No. 15/228,454, filed Aug. 4, 2016 (now U.S. Pat. No. 9,585,920, issued Mar. 7, 2017).

This application is a continuation-in-part of U.S. patent application Ser. No. 14/574,517 filed on Dec. 18, 2014, (now issued U.S. Pat. No. 9,408,880, issued Aug. 9, 2016), which claims priority of U.S. Provisional Patent Application Ser. Nos. 62/387,404, filed Dec. 24, 2015; 62/274,550, filed Jan. 4, 2016; and 62/275,341, filed Jan. 6, 2016.

This application is also a continuation-in-part application of U.S. patent application Ser. No. 14/611,458, filed Feb. 2, 2015 (now U.S. Pat. No. 10,398,209, issued Sep. 3, 2019), which is a continuation-in-part application of U.S. patent application Ser. No. 14/502,097, filed Sep. 30, 2014 (now issued U.S. Pat. No. 9,010,340, issuing on Apr. 21, 2015), which is a continuation of U.S. patent application Ser. No. 14/307,651, filed on Jun. 18, 2014 (now issued U.S. Pat. No. 8,936,030, issuing Jan. 20, 2015), which is a continuation-in-part application of U.S. patent application Ser. No. 14/079,054, filed Nov. 13, 2013 (now issued U.S. Pat. No. 8,757,173, issuing on Jun. 24, 2014), which is a continuation of U.S. patent application Ser. No. 13/425,913. filed Mar. 21, 2012 (now issued U.S. Pat. No. 8,584,685, issuing on Nov. 19, 2013), and claims priority of U.S. Provisional Patent Application Ser. No. 61/467,767, filed Mar. 25, 2011.

The entire disclosure of the prior applications are considered to be part of the disclosure of the accompanying application and are hereby incorporated by reference

FIELD OF THE INVENTION

A method and system to facilitate the growth of desired bacteria in a human's mouth by using a bioadhesive strip that has an encapsulated feature containing at least one bacteria and that has one of a pathogenic or toxic element excised using a clustered regularly interspaced short palindromic repeats (CRISPR)-CRISPR associated protein (Cas) system or a CRISPR from *Prevotella* and *Francisella* 1 (Cpf1) system, including oral strips that include at least one of xylitol, *Lachnospira, Veillonella, Faecalibacterium* and/or *Rothia* bacteria.

BACKGROUND OF THE INVENTION

All primary headaches are in need of better treatments. The most important primary headaches (i.e. independent disorders that are not caused by another disease) are migraine, tension-type headache and cluster headache. Migraine has a prevalence of 10% in the general population with a lifetime prevalence of 13% in men and 33% in women. Migraine is a highly disabling disease with high personal and social costs. To date, the precise mechanisms underlying the pathophysiology of migraine have remained elusive. Migraine strikes people during what are expected to be their most productive years: between ages 20 and 40 for most women, with a slightly higher age range for men. Migraine is typically characterized by unilateral onset of head pain, severe progressive intensity of pain, throbbing or pounding, and interference with the person's routine activities. Accompanying symptoms of photophobia (sensitivity to light) or phonosensitivity (intolerance to noise), as well as nausea and/or vomiting, are common, and often leads to the inability to perform daily tasks. A large portion of people with migraine often have no accompanying pain, their predominant symptom instead being vertigo (a spinning sensation) or dizziness/disequilibrium (balance loss), mental confusion, disorientation, dysarthria, visual distortion or altered visual clarity, or extremity paresis. Patients with migraine associated vertigo (MAV) are often seen by audiologists and vestibular rehabilitation therapists for evaluation and treatment. Because the exact mechanisms of migraine are still not completely understood, the management of migraine dizziness presently includes a combination of medications, vestibular rehabilitation, and lifestyle modifications that include limitation of risk factors associated with migraine (those related to diet, sleep, stress, exercise, and environmental factors).

Migraine is a disease associated with increased synthesis and release of calcitonin gene related peptide (CGRP) and a migraine attack can be blocked with CGRP antagonists. The actual pain is generated by nociceptors of trigeminal nerve endings in the dura. Low serotonin levels may sensitize the nociceptors of trigeminal neurons. Triptans and ergotamins, which decrease serotonin, are associated with relief of acute pain. In contrast, tricyclic antidepressants and selective serotonin and noradrenaline reuptake inhibitors, which are associated with increases in serotonin, are utilized for migraine prevention.

Migraine attacks can be triggered by intrinsic cerebral factors (e.g. calcitonin gene related peptide (CGRP) release), nitric oxide like tri-nitroglycerine, corticotrophin releasing hormone (stress), pro-inflammatory cytokines, and degranulation of mast cells located in the dura. While migraine has a genetic background, twin studies reveal that the cause of a majority of migraines appears to be due to environmental factors. The mechanism of triggering migraine is, however, still not understood. The cause of both migraines and chronic dizziness has eluded investigators for centuries and it therefore presents a truly long felt but unsolved mystery as to its causation and treatment.

SUMMARY OF THE INVENTION

One aspect of the present invention is therefore directed to addressing the causative agents involved in migraines and dizziness, instead of merely addressing the symptoms thereof. As can be seen from the prior art as discussed herein, the diagnosis and treatment of both migraines and dizziness have continued to be directed to symptoms, rather than to an underlying treatable cause. The present invention changes that focus and thus, provides both an understanding of causative agents and how best to treat individuals so that their maladies are addressed. The present inventors believe that there is an association between the occurrence of migraines and gastrointestinal (GI) disorders, including irritable bowel syndrome (IBS). People who regularly experience GI symptoms have a higher prevalence of headaches, with a stronger association with increasing headache frequency.

While not bound by theory, it is believed that the gut microbiota is an independent factor that contributes to systemic diseases, often involving the migration of stimulated immune cells, by systemic diffusion of microbial products or metabolites, or by bacterial translocation as a result of decreased intestinal barrier function. The brain and the GI tract are strongly connected via neural, endocrine, and immune pathways. The gut microbiota, as well as the oral microbiota, is associated with brain functions and neurological diseases like migraine.

Empirical data exists to reveal the association of migraines with disruptions of a person's microbiome. For example, children with a mother with a history of migraine are more likely to have infantile colic. Children with migraine are more likely to have experienced infantile colic compared to controls. Several studies demonstrated significant associations between migraine and celiac disease, inflammatory bowel disease, and IBS.

It is believed that the underlying mechanisms of migraine and GI diseases are both related to increased gut permeability and inflammation. In addition, it is believed that a person's oral microbiome is also responsible for migraines. Thus in several embodiments of the present invention, modification of the oral as well as (or solely) the gut microbiome is achieved to combat and address migraine occurrences.

The biological nitrogen cycle involves step-wise reduction of nitrogen oxides to ammonium salts and oxidation of ammonia back to nitrites and nitrates by plants and bacteria. The salivary bacterial reduction of nitrate to nitrite has been recognized as an important metabolic conversion in humans. Several enteric bacteria have also shown the ability of catalytic reduction of nitrate to ammonia via nitrite during dissimilatory respiration. Although to date the importance of this pathway in bacterial species colonizing the human intestine has been little studied, the present inventors submit that it is a major factor involved in the occurrence of migraines.

In addition to the connection between the gut microbiome and migraines, there is also believed to be a connection with the oral microbiome of an individual with various health conditions, including an association with dysbiosis of the oral microbiome and migraines.

Many biochemical, pharmacological, neuropathological, and experimental data suggest a role of nitric oxide in the pathogenesis of migraine. Nitric oxide (NO) is a very important molecule in the regulation of cerebral and extra cerebral cranial blood flow and arterial diameters. It is also involved in nociceptive processing. Glyceryl trinitrate (GTN), a pro-drug for NO, causes headache in normal volunteers and a so called delayed headache that fulfils criteria for migraine without aura in migraine sufferers. One aspect of the present invention is to prevent migraines via the inhibition of NO production; the blockade of steps in the NO-cGMP pathway; or the scavenging of NO. The pain signaling molecules, nitric oxide synthase (NOS) and calcitonin gene-related peptide (CGRP) are implicated in the pathophysiology of migraines.

Non-specific NOS inhibition and a specific neuronal NOS inhibitor have been found to attenuate neurogenic dural vasodilation. Interestingly, specific inducible and endothelial NOS inhibitors had no effect. Non-vascular inducible NOS inhibitors have been shown unable to abort or prevent migraine. The present inventors submit that this leaves neuronal NOS inhibition and bacterial NOS inhibition (bNOS) as candidates for therapy, with the latter being considered the primary causative agents in preventing migraines.

Neurons in the trigeminocervical complex are the major relay neurons and are the neural substrates of head pain. NO production in the TCC and potentially other areas of the brain may be involved in triggering migraines, and therefore blocking NO production is believed to be therapeutic.

The nitric oxide synthase inhibitor NG-monomethyi-L-arginine (L-NMMA) may be employed in several embodiments of the present invention. Blockade of nitric oxide synthases (NOS) by L-NMMA effectively treats attacks of migraine without aura. Similar results have been obtained for chronic tension-type headache and cluster headache.

Inhibition of the breakdown of cGMP also provokes migraine in sufferers, indicating that cGMP is the effector of NO-induced migraine. Several relationships exist between NO, calcitonin gene-related peptide and other molecules important in migraine. Also, ion channels, particularly the K(ATP) channels, are important for the action of NO.

NO donors and their ability to trigger migraine in patients is well known and so nitric oxide synthase (NOS) inhibitors have been explored for the treatment of migraine. While NO donors are known to cause vasodilation, they also cause activation of neurons in the trigeminocervical complex of the brain that are not vascular related, as well as other areas of the brain related to migraine. Thus, the present inventors submit that non-vascular mechanisms are involved and that non-vascular NOS inhibitors are efficacious in the treatment of migraines.

Nitric oxide synthases (NOSs) are multidomain metalloproteins first identified in mammals as being responsible for the synthesis of the wide-spread signaling and protective agent nitric oxide (NO). Nitric oxide synthases are heme-based monooxygenases that oxidize L-arginine to nitric oxide (NO), a signaling molecule and cytotoxic agent in higher organisms. NO is one of the main inflammatory mediators involved in both inflammation and angiogenesis. NO can be synthesized by three different isoforms of NO synthase: neuronal (nNOS), endothelial (eNOS), and inducible (iNOS) synthases. NO production due to cytokine-induced expression of inducible nitric oxide synthase (iNOS) is largely involved in the pathophysiology of inflammation.

Although NOS-like activity has been reported in many bacteria, only a few bacterial homologs of mammalian NOSs (mNOSs) have been characterized to date. Nitric oxide synthases (NOSs) play an essential role in synthesizing nitric oxide (NO) by oxidizing l-arginine. NO is a significant mediator in cellular signaling pathways. It serves as a crucial regulator in insulin secretion, vascular tone, peristalsis, angiogenesis, neural development and inflammation. Due to its important role, the inhibition of these vital enzymes provides therapeutic applications that target NOSs.

Over the past 10 years, prokaryotic proteins that are homologous to animal NOSs have been identified and characterized, both in terms of enzymology and biological function. In contrast to mNOSs, which possess both a catalytic and a reductase domain, the bacterial enzymes lack reductase domains and require the supply of suitable reductants to produce NO. A notable exception is a NOS from a gram-negative bacterium that contains a new type of reductase module.

Bacterial NOSs seem to have functions that differ from those of mNOSs, including nitration of different metabolites and protection against oxidative stress. Bacterial NOSs provide a better understanding of the mechanism of NO synthesis and unveil a variety of new functions for NO in microbes.

In one embodiment, the lactic acid bacterium *Lactobacillus reuteri* is employed as it is believed that by doing so, one is able to induce oxytocin, preferably in a manner that offers a sustained induction of oxytocin, unlike the short effects achieved using intranasal oxytocin sprays, etc. Thus, one aspect of the present invention relates to the employment of probiotics-induced oxytocin to reduce migraine symptoms, especially in the form of an oral adhesive strip as further described herein.

Other embodiments relate to the employment of calcitonin gene-related peptide (CGRP) as a major player in treating migraines. In various embodiments, CGRP triggers a chain of events such that increased amounts of CGRP released at the start of a migraine sensitize the trigeminal nerve to what are normally innocuous signals, resulting in inflammation in the nerves that is relayed to the brain as a pain signal and in such a manner, stop headaches from outside the central nervous system, believed to be active on the trigeminal connections into the brain rather than the brain itself. It is further believed that there is often a fairly massive change in the permeability of the blood-brain barrier during a migraine attack and may have an effect on certain sections of the brainstem that are not believed to be as well protected by the blood-brain barrier. As is the case with autism, it is believed that a gut brain inter-relationship dysbiosis is caused by a lowered *Lactobacillus* spp. and decreased number of *Clostridium* spp. populations in an individual's gut microbiome. Thus, restoring the gut microbiome with appropriate levels of particular bacteria species as set forth herein is one aspect of the present invention. In addition, in various embodiments, the maintenance of desired populations in the gut is achieved via the employment of fibre that is essential for the fostering of a healthy gut microbiome once established so that the beneficial bacteria have a food source other than the mucosa proteins that protect the tissue of the gut. In preferred embodiments approximately 6 g/fibre/day is administered to an individual as it is believed that by doing so one is able to increase the numbers of bifidobacteria in the gut microbiome and thus, increase desired fermentation by increasing the number and maintenance of both Bifidobacteriaceae and Lactobacteriaceae families. In preferred embodiments, a diet rich in plant polysaccharides (i.e., fiber) is employed to confer protection against various ailments associated with the gut microbiome dysbiosis, including not only migraines, but also cardiovascular disease (CVD). Such benefits are believed to be derived from the interactions between carbohydrates that reach the distal gut and microbes via production of short chain fatty acids (SOFA, e.g., acetate, propionate and butyrate). Thus, in various embodiments, in addition to the administration of beneficial bacteria as described herein wither to the gut or the oral microbiome of an individual (or both) the consumption of a diet high in fibre is employed to increase microbiota populations to generate short chain fatty acids (SCFAs) such as acetate, which has a protective role in inflammatory diseases. Such a diet is further believed to attenuate the development of cardiac fibrosis due to the belief that inflammation is also implicated in cardiac remodelling. Thus, a high fibre diet, especially one that includes increased levels of acetate, is believed to not only reduce the incidences of migraine, but to further result in significantly less cardiac hypertrophy, perivascular and interstitial cardiac fibrosis, and improved cardiac function. It is further believed that the protective effects of high fibre and acetate are accompanied by a decrease in the ratio of bacteria from the phylum Firmicutes compared to Bacteroidetes. In addition to the association of the gut and the brain as it relates to the incidence of migraines, there is also a gut-heart connection and by employing similar efforts to address the dysbiosis of an individuals' gut and oral microbiomes, another aspect of the present invention is directed to addressing and significantly preventing the occurrence of heart disease.

In situations where there is insufficient fiber for the beneficial bacteria to consume, the bacteria end up eroding the mucus of the gut and leads to epithelial access by mucosal pathogens. It is believed that there is an increase in the amount of calcitonin gene-related peptide released at the start of a migraine that sensitizes the trigeminal nerve to what are normally innocuous signals, resulting in inflammation in the nerves that is relayed to the brain as a pain signal. Thus, one aspect of the present invention relates to the ability to affect the trigeminal connections into the brain, rather than the brain itself, and to do so by modifying the type, number and maintenance of desired bacteria in an individual's gut and oral microbiome. In addition to migraine headaches, other aspects of the invention are directed more generally to addressing other pain related conditions, including but not limited to fibromyalgia, cluster headaches, etc.

Therefore, certain embodiments of the present invention are directed to a method of reducing the likelihood of migraine headaches by providing to an individual in need thereof a buccal bioadhesive strip, with such strip having a first and second side and having a surface comprising a pattern defined by a plurality of spaced apart features each having at least one microscale dimension and having at least one neighboring feature having a substantially different geometry. Preferably the average spacing between adjacent ones of such features is between 0.5 and 5 .mu.m. FIG. 2(*a*)-(*d*) illustrate some exemplary surface architectural patterns according to the invention.

A bioadhesive is employed that is adapted to bind to a mucosal membrane for at least 1 hour while inside an individual's mouth. Preferably the strip includes xylitol. In other embodiments, the strip includes an encapsulated feature containing a desired bacteria, preferably selected from the group consisting of *Lachnospira, Veillonella, Faecalibacterium* and *Rothia*. Still other embodiments include an antibody on the strip to a calcitonin gene-related peptide. The strip(s) may further include *Lactobacillus* spp.

Preferably, methods of the present invention further include administering a diet of at least 6 g/fibre/day to an individual so as to increase the numbers of *bifidobacteria* in the gut microbiome of the individual. Such a diet should preferably include a high fibre diet that includes acetate, especially in an amount sufficient to decrease the ratio of bacteria in the individual's oral cavity from the phylum Firmicutes compared to Bacteroidetes. It is preferred to increase the number of both Bifidobacteriaceae and Lactobacteriaceae bacteria. Other embodiments increase the population of desired bacteria by including *Enterococcus faecium* on the strip. It is preferred to remove from the oral cavity of the individual gram negative bacteria associated with periodontitis, and within 2 hours thereof, to provide the individual with the strip. Still other embodiments include a strip that includes *Lactobacillus reuteri* bacteria to induce a sustained induction of oxytocin, and providing the individual with an amount of antibiotic sufficient to reduce the number of undesired bacteria in the oral cavity. Prior to the use of the strip, an antibiotic selected from the group consisting of tetracycline hydrochloride, doxycycline, and minocycline is used to reduce the number of undesired bacteria in the oral cavity. One objective is to retard the growth conditions for spirochetes and *P. gingivalis*, believed to be associated with migraine headaches. In still other embodiments, *Veillonella* and/or *Prevotella* bacteria is provided on the strip. As one of skill in the art will appreciate, the strip may be made to include at least one polymer selected from the group consisting of pullulan, hydroxypropylmethyl cellulose, hydroxyethyl cellulose, hydroxypropyl cellulose, polyvinyl pyrrolidone, carboxymethyl cellulose, polyvinyl alcohol, sodium alginate, polyethylene glycol, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, levan, elsinan, collagen, gelatin, zein, gluten, soy protein isolate, whey protein isolate, casein and mixtures thereof. Preferably, the strip includes at least 0.2% xylitol by weight. In certain embodiments, the strip comprises bioluminescent material. Preferably the strip is dissolvable in a person's mouth within a period of 1 hour. In certain preferred embodiments, the strip has least one encapsulated feature that contains an agent selected from the group consisting of an antibiotic; lactic acid bacteria; and xylitol, e.g. at least 200 mg of xylitol. Such a frangible capsule may be constructed so that it may be broken by the individual pressing against said strip with the individual's tongue.

Still other embodiments of the present invention are directed to addressing the incidence of migraines and cluster headaches using bacteria of the oral cavity and gut of an individual. Microbes, among others in the digestive tract, are capable of oxidizing alcohol to acetaldehyde. Compositions containing one or more cysteines as active agents have been shown to bind acetaldehyde. These active agents have been found to also be capable of breaking down biofilms formed by some microbes, particularly in the stomach. One aspect of the present invention is therefore directed to reducing the likelihood of headaches, including not only migraines, but also cluster headaches. Thus, several embodiments employ microbes, preferably particular bacterial species as set forth herein, to assist in decreasing the amount of acetaldehyde in the body of an individual who suffers from such headaches. This can be achieved by employing cysteine generating microbes that are effective in reducing the amount of acetaldehydes. Other microbes are also effective in degrading acetaldehydes.

While migraines are diagnosed more often in women, cluster headaches are more prevalent in men. Cluster headache is a neurological disease that involves, as its most prominent feature, excruciating unilateral headaches of extreme intensity. "Cluster" refers to the tendency of these headaches to occur periodically, with active periods interrupted by spontaneous remissions. The cause of the disease is currently unknown. Cluster headaches are sometimes classified as vascular headaches. The intense pain has been suggested to be linked with the dilation of blood vessels which creates pressure on the trigeminal nerve. Cluster headache episodes are known to be triggered by factors, such as alcohol consumption. Patients who are sensitive to alcohol note that attacks are triggered within 5 to 45 minutes after the ingestion of modest amounts of alcohol, usually being less than a single cocktail or glass of wine. Alcohol triggers attacks in 70 to 80% of exposures. Microbial metabolism may contribute to the toxicity of alcohol, especially in the gastrointestinal tract, where aerobic and facultative anaerobic bacteria convert ethanol to acetaldehyde. Indeed, acetaldehyde is known to be a highly toxic and pro-carcinogenic compound with various negative effects, ranging from DNA damage and impaired DNA excision repair to the degradation of folate. Thus, one aspect of various embodiments of the present invention is directed to providing particular bacteria to a person who consumes alcohol in a manner that such bacteria may ameliorate the accumulation of acetaldehyde. In certain embodiments, bacteria are employed to degrade acetaldehyde, such bacteria preferably having an aldehyde dehydrogenase, such as bacteria of the genus *Saccharomyces* and/or a threonine aldolase derived from *Escherichia coli*. Employment of CRISPR-Cas systems to incorporate the genes of such bacteria into other bacteria as set forth herein forms various other embodiments of the present invention. Thus, use of bacteria in the oral cavity, as well as in the gut microbiome of an individual, are employed to degrade acetaldehyde and thus reduce the incidence of migraines and cluster headaches. While many of the embodiments described herein are principally directed to a method and system for addressing the terrible pain occasioned by headaches caused by migraines and cluster headaches, one may further appreciate other aspects of the invention as being directed to hangover remedies as the ability to degrade alcohol and acetaldehyde to remedy the effects of consuming too much alcohol: thus introducing "Hangover Strips" in addition to Headache Strips as described herein.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, figures, etc. will provide a basis for the scope of the present invention as it may be claimed now and in future applications.

BRIEF DESCRIPTION OF THE FIGURES

FIG. 4 is an illustration of a pre-made sheet of strips that can be disassociated with the sheet and then applied to mucosal membranes.

FIG. 5 is a side view of one embodiment of a strip having an outer layer, an adhesive layer, a layer with an encapsulated agent contained there between.

FIG. 6 is a side view of one embodiment where the encapsulated agent is encapsulated into small beads that are frangible via pressure of an individual's tongue pressing against the strip so as to force it into the roof of a person's mouth.

DETAILED DESCRIPTION OF VARIOUS EMBODIMENTS OF THE INVENTION

Figure 1:
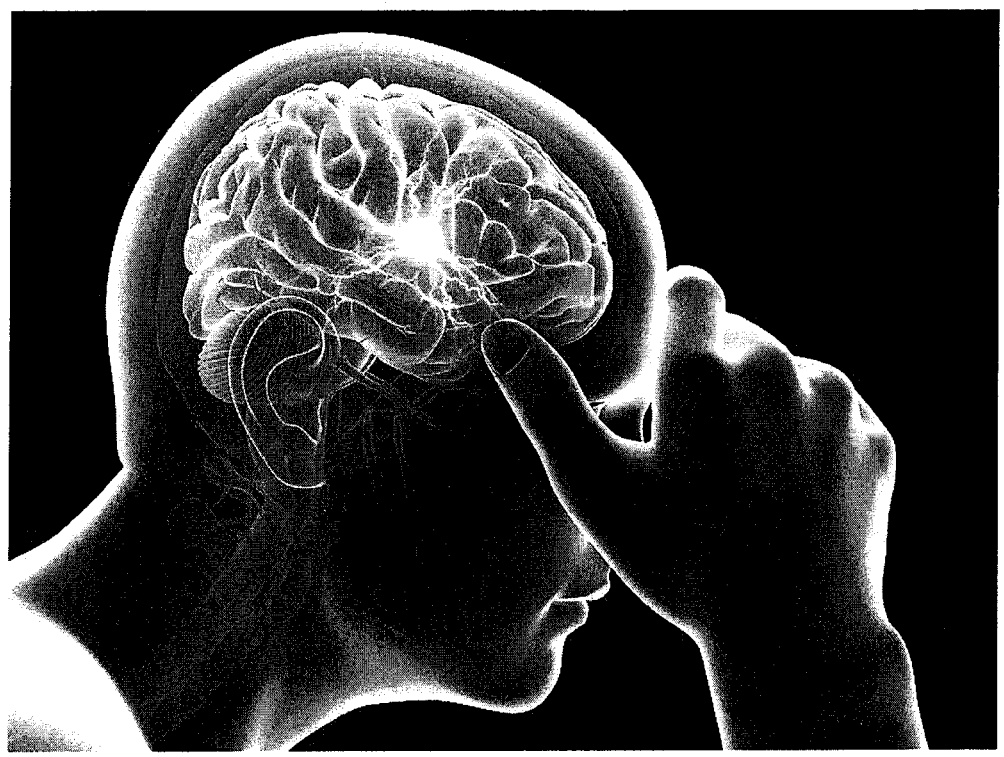
FIG. 1 is an illustration of a person experiencing the pain of a migraine headache.
Figure 2A:
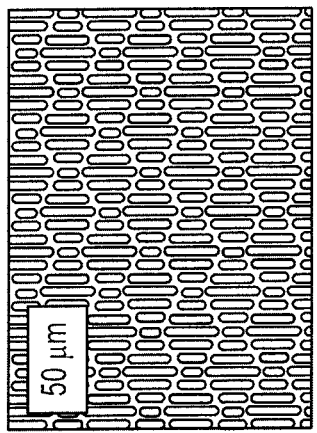
FIG. 2(*a*)-(*d*) illustrate some exemplary surface architectural patterns according to the invention.
Figure 2B:
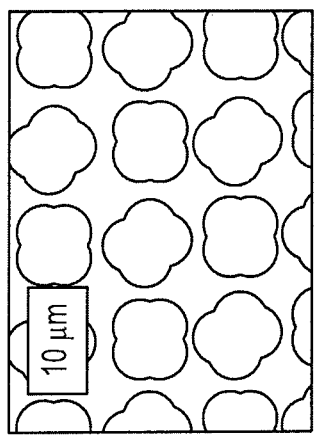
Figure 2C:
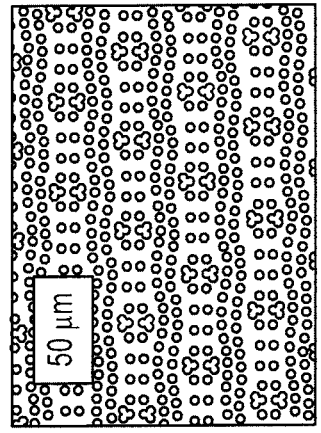
Figure 2D:
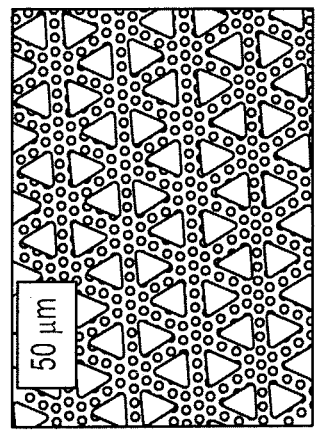
Figure 3:
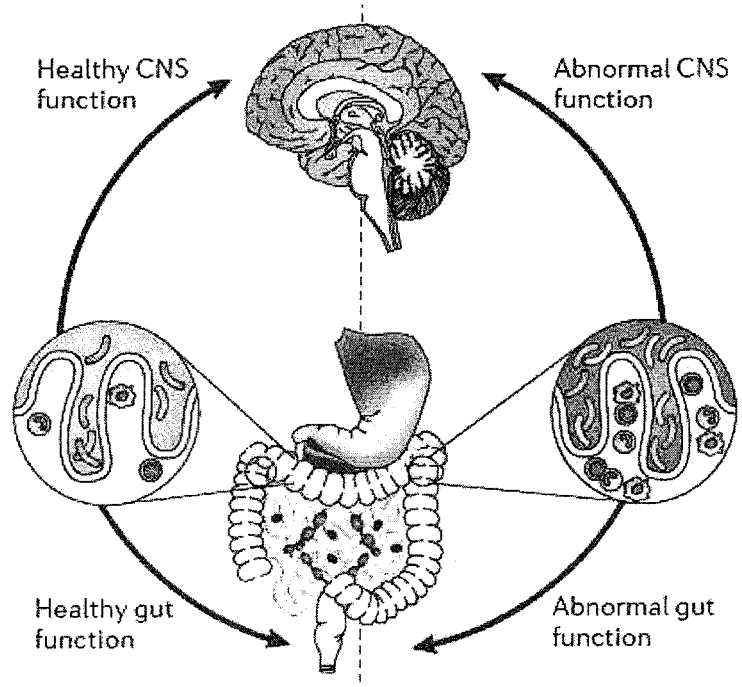
FIG. 3 is an illustration of how beneficial bacteria in an individual's gut microbiome relates to the health of the central nervous system, as well as how dysbiosis of the gut microbiome relates to various problems experienced with the central nervous system including the occurrences of migraine headaches.

There is a higher prevalence of headaches among people who regularly experience GI symptoms compared to control groups without GI complaints. Colic has also been suggested as an early life expression of migraine and thus, the present inventors believe that there is an association between migraine and infantile colic. Infantile colic is a common cause of inconsolable crying during the first months of life with incidence rates ranging from 5 to 19%. Mothers with a history of migraine were 2.6 times as likely to have colic as infants than those mothers without a maternal history of migraine. Infants with abdominal colic have a lower intestinal microbiota diversity and stability as compared to control infants in the first weeks of life. Children with migraines are more likely to have experienced infantile colic compared with controls.

Irritable bowel syndrome (IBS) is a functional bowel disorder characterized by abdominal pain, bloating, discomfort, and marked changes in bowel habits. IBS and migraine are both 2-3 times more prevalent in women than in men. IBS has been shown to be a disorder with an increased intestinal permeability and this permeability increases with more severe IBS symptoms.

The present inventors contend that there is a strong relationship between GI disorders and migraine. One of the links between inflammatory diseases and migraine are enhanced pro-inflammatory immune responses. A strong trigger of pro-inflammatory immune responses is the leakage of lipopolysaccharides (LPS) from the intestinal lumen into the circulation. Enhanced levels of LPS can enter the circulation when the intestinal permeability is increased. Depending on genetic susceptibility, pro-inflammatory responses can occur in different parts of the body, e.g., in case of migraine on the nociceptors of the trigeminal nerve.

Gut permeability and inflammation are bi-directionally related; increased permeability can cause inflammation, but inflammation can also cause increased gut permeability. An increased gut permeability, and thereby increased translocation of LPS, can be caused by multiple factors like medicines, exercise, mast cell activation, high fat diet, stress, etc. The most used method to measure epithelial barrier function is with the lactulose/mannitol test. Mannitol is transported via the transcellular pathway whereas lactulose is absorbed through the paracellular pathway. In case of increased permeability, more lactulose passes the barrier and eventually ends up in the urine. Therefore, an increase in intestinal permeability is characterized by an increased ratio of lactulose/mannitol. It is believed that the reduction of the permeability of the intestine results in relief of migraine in the subgroup of patients in whom intestinal permeability plays a role in the disease. Subjects with food allergies have an increased intestinal permeability compared with healthy controls.

The brain-gut-microbiome axis is the bidirectional communication between the central nervous system and the gastrointestinal tract. The underlying mechanisms include increased gut permeability and inflammation. Probiotics decrease intestinal permeability as well as inflammation, and therefore reduce the frequency and/or intensity of migraine attacks. In accordance with various embodiments of the present invention, a combination of various bacterial strains may be employed to combat migraines and dizziness including: *Lactobacillus acidophilus* DDS-1, *Lactobacillus bulgaricus*, *Enterococcus faecium* and *Bifidobacterium bifidum*.

Probiotics are living microorganisms that have beneficial effects on the health of the host. The most used probiotics are lactobacilli and bifidobacteria. Effects of probiotics are dependent on the used species and strain. Probiotics in the treatment of GI disorders is believed effective due to the strengthening of the intestinal barrier of a person. Probiotics have shown to be able to improve the epithelial barrier function via different mechanisms. Similarly, probiotics play a role in maintaining or improving gut barrier function as well as in migraine patients with an enhanced intestinal permeability.

Migraine prevalence is associated with gastrointestinal disorders. A combination of different probiotics (*Lactobacillus acidophilus, Lactobacillus bulgaricus, Enterococcus faecium*, and *Bifidobacterium bifidum*) can be employed for such purpose. Certain methods of the present invention are directed to probiotic formulations included on or encapsulated into a strip of the present invention such that the desired bacteria is delivered to the mucosal membrane. Such strips may include one or more desired bacterial species, useful for promoting or maintaining the health and general well-being of humans, including but not limited to the following: organisms of *Enterococcus faecium*, including strain NCIMB 40371, deposited on 25 Feb. 1991 in accordance with the provisions of the Budapest Treaty, in the National Collections of Industrial and Marine Bacteria Limited, Aberdeen, under Accession No. NCIMB 40371.

Dental plaque, a sticky colorless film, is caused by bacterial deposits accumulating on tooth or implant surfaces along the gingival margins and results in the destruction of tooth-supporting tissues. Dental plaque formation starts in cracks, grooves and surface roughness on teeth and/or dental implants. In any given plaque sample, it is not uncommon to detect 30 or more bacterial species. Biofilms that colonizes the tooth surface may be among the most complex biofilms that exist in nature. The bacteria associated with periodontal diseases reside in biofilms both above and below the gingival margin. The supragingival biofilm is attached to the tooth or the implant and predominated by *Actinomyces* species. The subgingival biofilm is typically more complex and can either attach to the tooth or implant, or to the gingival tissue. Three microbe species are believed to be main players in the cause the periodontal diseases: *A. actinomycetemcomitans, P. gingivalis* and *B. forsythus*. Also, *F. nucleatum, Campylobacter rectus, P. Intermedia, P. nigrescens, Eubacterium nodatum, P. micros* and various spirochetes have been singled out that may also be important species in periodontal disease.

The destruction of tooth-supporting tissues results in a deepening of the space (periodontal pocket) between the root of the tooth and the gum tissue. Second to tooth decay, periodontal diseases are the most frequent oral diseases and may lead to partial or complete tooth or bone loss. It has been estimated that they affect as much as between 70-90% of the world population, and they are the major cause of tooth loss in people over 35 years of age. In periodontitis the infection has progressed to involve the oral tissues which retain the teeth in the jawbone. If untreated, periodontitis ultimately leads to loss of the affected tooth. Chronic periodontitis, the most frequently occurring form of periodontitis, results in inflammation within the supporting tissues of the teeth, progressive loss of attachment as well as progressive alveolar bone resorption. This form of periodontitis is characterized by pocket formation and/or recession of the gingiva. As the destruction advances, the mobility and movement of teeth increase, finally causing spontaneous loss of a tooth or a necessity of tooth extraction. Treatment of periodontal diseases usually involves the removal of bacterial deposits and dental calculus. However, it is difficult to have full access for treating deeper periodontal pockets, resulting in remaining bacteria that may re-infect the tissue.

$O_2$ and NO act as environmental cues that trigger the coordinated expression of virulence genes and metabolic adaptations necessary for survival within a host. NO concentrations may be produced by fecal microbiota from nitrate, with the nitrate being reduced to ammonium by the dissimilatory nitrate reduction to ammonium (DNRA) pathway. Gastrointestinal microbiota can generate substantial amounts of NO by DNRA, rather than by the generally accepted denitrification or L-arginine pathway. Bacterial nitrate reduction to ammonia, as well as the related NO formation in the gut, is believed to be an important aspect of the overall mammalian nitrate/nitrite/NO metabolism, demonstrating how the microbiome links diet and health.

Biofilm initiated diseases are by no means unique to the oral cavity. Approximately 65% of infections that affect the human are caused by organisms growing in biofilms. These include dental caries, periodontal disease, otitis media, musculoskeletal infections, necrotizing fasciitis, biliary tract infection, osteomyelitis, bacterial prostatitis, native valve endocarditis, meloidosis, prosthetic as well as orthopedic complications and cystic fibrosis pneumonia. Characteristics are persistence and chronicity of the infections as well as the difficulty in eradication.

The present inventors also submit that migraine headache is a precursor to Alzheimer's disease as it is associated with the same causative factor, namely periodontitis. As such, and as addressed in the present description and in co-pending cases, incorporated herein by this reference, the treatment of migraines by addressing the breakdown of biofilms so as to kill particular bacteria, including spirochetes found in the oral cavity. Strips of the present invention can be employed to position agents, including beneficial bacteria, bacteria modified employing CRISPR-Cas systems, and the use of antibiotics effective against various gram negative bacteria, including but not limited to spirochetes, forming various embodiments of the present invention. There are several aspects that are similar, if not the same in the processes of both illnesses. Risk factors common for patients suffering from each disorder include visual dysfunction, depression, lethargy, mood changes, sense of pain to non-painful stimuli, inability to produce purposeful coordinated movements, and in women changes in ovarian hormone levels. The neurotransmitter systems and inflammatory processes throughout the body are directly related to variations in estrogen and progesterone levels.

One aspect of the present invention relates to the removal from the oral cavity of disease causing bacteria, principally gram negative bacteria associated with periodontitis, followed by antibiotic treatments to ensure such bacteria removal from the oral cavity, and then followed up within hours with a regimen that includes the purposeful exposure of a person's oral cavity with beneficial bacteria, thus promoting the avoidance of future periodontal disease. The strips as described herein can be used for each or a combination of such functions. The correct formation of a beneficial biofilm is thus one aspect of the present invention. If this last step is not implemented, then there will invariably be a biofilm generated, but often one that is not beneficial to the person, and one that could lead again to periodontitis. Thus, the purposeful exposure and administration of select bacterial species is one objective of the present invention.

Streptococci constitute 60 to 90% of the bacteria that colonize the teeth in the first 4 hours after professional cleaning. Other early colonizers include *Actinomyces* spp., *Capnocytophaga* spp., *Eikenella* spp., *Haemophilus* spp., *Prevotella* spp., *Propionibacterium* spp., and *Veillonella* spp.

Antibiotics can be prescribed at a low dose for longer term use, or as a short-term medication to deter bacteria from re-colonizing. Preferably, in various embodiments of the present invention, strips that contain appropriate amounts and types of antibiotics are employed to adjust the population of the oral and the gut microbiome of a person to alleviate migraine and dizziness symptoms. Incorporated by reference in its entirety is U.S. Pat. No. 9,445,936, directed to the use of mucosal strips, and especially oral strips, that can be provided with various bacterial components to adjust and modify the oral microbiome of an individual. It is sometimes advisable to undergo a treatment with antibiotics so as to reduce the number of other undesired bacteria in the oral cavity, prior to the use of the strips having the desired bacteria included thereon. Antibiotics which include tetracycline hydrochloride, doxycycline, and minocycline are the primary drugs used in periodontal treatment and that are preferred for use in the strips as described herein. Such strips with these agents have antibacterial properties, reduce inflammation and block collagenase (a protein which destroys the connective tissue). Metronidazole is generally used in combination with amoxicillin or tetracycline to combat inflammation and bacterial growth in severe or chronic periodontitis and the use of these antibiotics on or encapsulated on strips of the present invention permit selective administration to the oral cavity in a manner that has never been done before. In preferred embodiments, the direct delivery of antibiotics to the surfaces of the gums by using the strips as described herein is preferred and are extremely effective when used after scaling and root planing procedures. Among the various existing agents that can be incorporated into the strips of the present invention, especially those that encapsulate such agents such that a person can self-administer the agents via tongue pressure applied to frangible shells containing such material, are as follows: a doxycycline gel that conforms to the contours of gum surfaces and solidifies over them; Chlorhexidine, a powerful antibacterial antiseptic; tetracycline hydrochloride; metronidazole; and Minocycline. In certain embodiments, the strips as described herein are employed to modify the oral microbiome of an individual to treat migraines. Thus, a buccal bioadhesive strip is preferably used that has a first and second side, with the first side having a surface comprising a pattern defined by a plurality of spaced apart features each having at least one microscale dimension and having at least one neighboring feature having a substantially different geometry, and wherein an average spacing between adjacent ones of said features is between 0.5 and 5 .mu.m in at least a portion of the surface. The first side has a bioadhesive that is adapted to bind to a mucosal membrane for at least 1 hour while inside a person's mouth. The strip may, for example, extend over a majority of the soft palate and preferably includes xylitol. Other embodiments have the strip including at least one encapsulated pocket containing one of an analgesic, a lactic acid bacteria, or another of the desired bacteria as described herein. FIG. 4 is an illustration of a pre-made sheet 100 of strips 120 that can be disassociated with the sheet and then applied to mucosal membranes. FIG. 5 is a side view of one embodiment of a strip 120 having an outer layer, an adhesive layer, a layer with an encapsulated agent contained there between. FIG. 6 is a side view of one embodiment where the encapsulated agent 110 is encapsulated into small beads that are frangible via pressure of an individual's tongue pressing against the strip so as to force it into the roof of a person's mouth.

A major problem with bacterial biofilms is the inability of the host immune system and/or antibiotics and other antimicrobials to gain access to the bacteria protected within the biofilm. Thus, a need exists to break through the protective barrier of biofilms to treat or kill the associated bacterial infections as the biofilm can act as a reservoir for future acute infections often with lethal consequences. Although a laser can be used to kill bacteria, this method in isolation does not necessarily remove the bacteria, and thus a biofilm can remain on the implant which can hinder osseointegration and may act as a source of later infection. Antimicrobial agents are not effective at normal dosage, as the minimum inhibitory concentration for antibiotics for an organism in biofilm mode might be 1000-1500 times higher than for the same organism in the planktonic state. Periodontal diseases are infections caused by microorganisms that colonize the tooth or implant surface at or below the gingival margin. While these infections have many properties in common with other infectious diseases, they exhibit unique properties conferred by their site of colonization and the nature of the environment in which they reside. The onset of the diseases is usually delayed for prolonged periods of time after initial colonization by the pathogens.

Thus certain embodiments of the present invention are directed to a prophylactic method for treating chronic migraine comprising (after the above referenced steps of removing pathogenic bacteria associated with a person's periodontitis, including after antibiotic applications) administering on a daily basis to humans a composition comprising: probiotics selected from the group consisting DDS-1 strain of *Lactobacillus acidophilus, Lactobacillus bulgaricus, Lactobacillus johnsonii, Bifidobacterium bifidum* and *Enterococcus faecium* in a unit dosage amount ranging from 1000 to 3000 mg. Useful probiotic agents include (in addition to the numerous others referenced herein) *Bifidobacterium* sp. or *Lactobacillus* species or strains, e.g., *L. acidophilus, L. rhamnosus, L. plantarum, L. reuteri, L. paracasei* subsp. *paracasei,* or *L. casei Shirota; Lachnospira, Veillonella, Faecalibacterium* and *Rothia,* and *Prevotella.*

Human oral bacteria interact with theft environment by attaching to surfaces and establishing mixed-species communities. Several oral bacterial species are amenable to genetic manipulation for molecular characterization of communication both among bacteria and between bacteria and the host. Due to the dynamics of growth and adherence, the bacterial populations in the oral cavity are constantly changing, even during the intervals between normal daily oral hygiene treatments. The various species within oral biofilms function as a coordinated community that uses intra- and interspecies communication.

Development of the oral microbial community involves competition as well as cooperation among the 500 species that compose this community, including the following: *Actinobacillus actinomycetemcomitans, Actinomyces israelii, Actinomyces naeslundii, Capnocytophaga gingivalis, Capnocytophaga ochracea, Capnocytophaga sputigena, Eikenella corrodens, Eubacterium* spp., *Fusobacterium nucleatum, Haemophilus parainfluenzae, Porphyromonas gingivalis, Prevotella denticola, Prevotella intermedia, Prevotella loescheii, Propionibacterium acnes, Selenomonas flueggei, Streptococcus gordonii, Streptococcus mitis, Streptococcus oralis, Streptococcus sanguis, Treponema* spp., and *Veillonella atypica.* Although *F. nucleatum* is often considered a periodontal pathogen, it may instead contribute to maintaining homeostasis and improving host defense against true pathogens.

Competitive and cooperative mechanisms may be central to successful mixed species colonization as well as the proper succession of genera known to occur on teeth in both health and disease. Within the oral cavity, bacteria form multispecies communities that are distinguishable primarily by their location (supragingival versus subgingival versus epithelial). The subgingival community has the highest species richness and the greatest capacity for pathogenic outcome, such as periodontal tissue destruction.

It has been shown in vivo that veillonellae are not capable of colonizing the tooth surface without streptococci as metabolic partners and that larger populations of veillonellae develop in coculture with streptococci that recognize them as a coaggregation partner than in coculture with streptococci with which they do not coaggregate.

While migraines and Alzheimer's Disease share certain similarities in terms of bacterial and nerve passages of material to the brain, it is as yet unknown if the spirochetes believed responsible for the majority of AD is also associated with migraines and cluster headaches. About 60 oral species of *Treponema* have been identified, and spirochetes constitute a large percentage of the total oral bacterial numbers. Accordingly, a large *T. denticola* population could benefit greatly through interaction with a small *P. gingivalis* population. A stimulatory effect of *P. gingivalis* supernatant on *T. denticola* growth points to a synergistic interaction between *P. gingivalis* and other anaerobic bacteria such as oral spirochetes, and may be increased growth and increased virulence of these potential periodontal pathogens.

One aspect of the present invention is to avoid a large population of spirochetes in the oral cavity and one way of doing so involves limiting the population of other bacteria that spirochetes depend upon to thrive and grow. Thus, one aspect of the present invention is directed to the limitation or destruction or the retarding of growth conditions for spirochetes, which includes the limitation of the presence of *P. gingivalis.* Subtle regulation of gene expression in any organism within a community may lead to significant changes in the organism's ability to participate in community activities, such as use of community-formed metabolic end products as nutrients. Thus, interference with the biofilms relied upon for spirochetes growth and maintenance is one aspect of the present invention, which may be achieved via the use of oral strips of the present invention that have structural features thereon that deter bacteria growth, and that may also have antibiotics as well as beneficial bacteria residing thereon, and alternatively or in addition to, may have xylitol on the strip.

One aspect of the present invention is to trigger small changes in a person's oral and/or gut microbiome such that they cause large shifts in population composition and metabolic output of mixed-species communities. In certain embodiments, this is accomplished by inactivation of a gene (via CRISPR-Cas or CRISPR-Cpf1) involved in mixed-species community formation to cause a subtle variation in an organism's phenotype only during critical transitions in population composition and have no effect on population composition before or after the transition.

In still further particular embodiments, the *Treponema denticola* genome is modified to target the expression of particular chromosomal integrons, as it is the only human-associated bacterial species that harbors chromosomal integrons, with no integrons in other *Treponema* species being found. For example, in one particular embodiment of the present invention, genes from *Treponema* are modified to excise one or more virulence factors to address the progression of diseases, such as Alzheimer's disease, dizziness, migraines and cluster headaches, by addressing the causative factors of such diseases in the oral cavity of the person, prior to the full-blown development of such diseases. Chronic periodontitis is an inflammatory disease that is caused by the accumulation of bacteria in the form of a biofilm in the periodontal pocket. It can be treated with oral hygiene in conjunction with β-lactam antibiotics. Many oral anaerobic bacteria associated with chronic periodontal diseases have developed resistance to β-lactam antibiotics by virtue of their production of β-lactamase enzymes. Using CRISPR-Cas techniques to delete virulence factors and to restore antibiotic sensitivity to permit use of known effective antibiotics, is one aspect of the present invention.

A high prevalence of β-lactamase-producing oral anaerobic bacteria has been found in patients with chronic periodontitis. As a large percentage of bacteria carry a gene that renders them resistant to β-lactam antibiotics, alternative antimicrobial agents should be employed in patients that are non-responsive to β-lactam antibiotics. Use of CRISPR-Cas systems to render particular bacteria susceptible to such antibiotics is one aspect of the present invention, as well as the purposeful exposure of a person's oral cavity (after existing bacterial flora has been substantially removed) to replace the flora with a CRISPR-Cas system modified bacteria culture such that the control over the oral population of bacteria can be achieved, such as by rendering such bacteria susceptible to antibiotics.

Yet another aspect of the present set invention is directed to the employment of phospholipid vesicles in addressing desired modifications to the human microbiome, and in particular to the oral microbiome, Bacterial membrane vesicles (MVs), released by many bacteria, mainly consist of the cell membrane and typically range from 20 to 400 nm in size. Bacterial MVs are involved in several biological functions, such as delivery of cargo, virulence and gene transfer. Although MV biogenesis and biological roles are yet to be fully understood, one aspect of the present invention relates to the oenetic engineering of such MVs to tailor them for applications in drug delivery systems and nanobiocatalysts, MV vaccines, etc. MVs have been found to mediate diverse functions, including promoting pathogenesis, enabling bacterial survival during stress conditions and regulating microbial interactions within bacterial communities. Modification and increased expression of such vesicles, including the ability to employ CRISPR-Cas systems to affect the transfer of desired components to the oral cavity via such vesicles, is part of various embodiments of the present invention. The existence of membrane vesicles increases the complexity involved in the diffusion of secreted substances during microbial interactions and MV secretion has been observed in Gram-negative bacteria as well as in other prokaryotes, including Gram-positive bacteria and archaea. MVs contain proteins, DNA, RNA and quorum sensing signals, and these substances are transferred to cells. MVs have unique characteristics, including the fact that several chemical substances are highly concentrated in MVs, the interior substances in MVs are protected against environmental stresses, and MVs play a role in effectively delivering these substances to cells.

In one particular aspect of the present invention, MVs of human specific pathogens are employed to incapacitate the pathogenic nature of such bacteria. The association between MVs and eukaryotic cells has been studied in pathogenic bacteria, and MVs secreted from pathogens transfer virulent factors to cells. In particular, specific proteins localized on the surface of MVs increase the association with epithelial cells, believed to be due to increasing the association of MV lipopolysaccharide with cells.

Microbial predation using MVs occurs when virulent factors or peptidoglycan hydrolytic enzymes contained in MVs are transferred to other bacterial cells. It has been suggested that the mechanism of bacterial lysis via MVs secreted from Gram-negative bacteria differs in whether recipient cells are Gram-negative or positive. Thus, cell-to-cell communications in the oral cavity involve microbes intricately communicating through methods using MVs, thereby influencing interspecies networks, microbial community organization and ecosystem dynamics. Employment of the specially surfaced structured strips of the present invention may be used to alter the population of an individual's microbiome in a manner that can later the progression of bacterial related diseases, including migraines, cluster headaches and Alzheimer's. With respect to treatment, several embodiments employ Graphene oxide nanosheets, and especially in the form of the strips as described herein, to deliver an effective antibacterial material against dental pathogens, including especially *Treponema denticola*.

As discussed herein, there is an association with periodontitis and migraines. Thus, one aspect of certain embodiments of the present invention relate to a series of steps to be undertaken to address the killing and elimination of certain gram negative bacteria that are associated with periodontitis, followed by the purposeful application of a composition having beneficial bacteria that are adapted to growth so as to populate a person's mouth and thus prevent the reestablishment of harmful bacteria that could, if permitted to persist in a person's mouth, lead to various maladies, including periodontitis, Alzheimer's disease, cluster headaches and migraines. In particular embodiments, strips are employed that have at least one encapsulated drug containing capsule that when broken or fractured, can release a predetermined amount of a drug, such as one effective to reduce if not eliminate certain gram negative bacteria and/or spirochetes that are believed responsible for periodontal disease, and in one preferred embodiment involves the use of metronidazole, preferably encapsulated or imbued onto a bioadhesive strip of the present invention. Certain embodiments of the present invention employ oral pharmaceutical compositions that include metronidazole, especially contained within a release layer of a bioadhesive strip that dissolves or erodes in the oral cavity.

Thus, in certain embodiments, the present invention provides an ability of a patient to purposefully cause the rupture of an encapsulated packet or pocket (e.g. a space in a strip that captures the agent of choice, which is released upon the rupture of such packet/pocket) that is associated with a strip that is adapted to be placed in association with a person's gums, with the encapsulated material preferably being an antibiotic, e.g. metronidazole, adapted to kill gram negative bacteria, and especially microbes associated as a causative agent in periodontitis.

Metronidazole is a nitroimidazole antibiotic with antibacterial activity against obligate anaerobic bacteria and certain protozoan parasites. The usual oral antibacterial therapies for treating pathologies have often given contradictory results. For instance, excessive dilution of the active ingredient has been observed in the intestinal lumen. This dilution is believed to be due to the premature release of the antibacterial agent from the pharmaceutical form even before reaching the duodenum such as in the stomach and in the immediate vicinity of the patient's pyloric valve. Similarly, in the oral cavity, use of metronidazole in a systemic fashion has limited results, as it does not persist in a concentrated enough form to kill undesired microbes that are entrenched in the gum regions of a person's mouth. Thus, in various embodiments of the present invention, metronidazole is provided in adhesive strips that are configured for providing the oral cavity with a sufficiently high level and dosage of the drug to accomplish the desired killing of certain bacterial species, including particular spirochetes such as *T. denticola*.

In another particular aspect, a genetically modified microbe, such as a bacteria of the species *T. denticola* and/or *Prevotella*, includes an inducible promoter directing expression of an essential protein and/or is modified such that expression of virulence factors are substantially reduced or eliminated. In certain embodiments, a composition comprises one or more genetically modified microbes, such as a bacteria of the species *T. denticola* and/or *Prevotella*, each of which are genetically modified, and especially by employment of CRISPR-Cas or Cpf1 systems to attenuate virulence factors, etc. CRISPR-Cas or Cpf1 modified microbes in which expression of an endogenous pathogenic protein is substantially reduced or eliminated in the one or more genetically modified bacteria include an inducible promoter regulating the expression of a virulence factor for such microbe.

Still other embodiments are directed to the use of bacteriophages modified to attack particular bacteria, especially *T. denticola* and/or *Prevotella*, to reduce the populations of one or the other in the oral cavity. In accordance with the present invention, native bacterial adaptive immune systems can be modified to thwart the conventional ability to confer immunity against bacteriophage infection. The CRISPR-Cas sequences, which are present in approximately 40% of eubacterial genomes and nearly all archaeal genomes sequenced to date, is employed to reverse the resistance to various antimicrobial agents such as small molecule antibiotics and bacteriophages.

Thus in certain embodiments, the innovative method is directed to decreasing the relative representation of a specific strain of bacteria, preferably *T. denticola* and/or *Prevotella*, within a heterogenous population of oral bacteria, comprising contacting the heterogenous population of oral bacteria with a bacteriophage comprising a polynucleotide that expresses (a) an RNA-directed DNA-binding polypeptide comprising a nuclease module; and (b) a targeting module comprising a guide RNA, wherein the targeting module tethers the RNA-directed DNA-binding polypeptide to a target DNA sequence within, thereby producing a double-strand break within the target sequence, wherein the target sequence is unique to the specific strain of *T. denticola* and/or *Prevotella* bacteria.

In certain embodiments of the present invention, delivery of beneficial bacteria, after the removal of pathogenic bacteria and also after use of the strip treatments as described herein (e.g. including the administration of local antibiotics to oral tissues), is achieved in a manner that comports with where such bacteria are normally located in a person's body. For example, many of the bacteria that confer protection against autoimmune diseases and that are otherwise believed to promote health in humans, and as described herein, are normally resident in the human mouth. For instance, one of the FLVR bacteria recently touted as being beneficial in the prevention of disease, namely *Veillonella*, is commonly found in a person's mouth, mostly living on the tongue and saliva. In various embodiments, selected bacteria, such as *Veillonella*, is purposefully presented on an oral strip that adheres to the mucosal membrane of a person.

In various embodiments of the present invention, bacterial species to be exposed to a person's oral (or in other embodiments, gut) microbiome, include those specifically modified by employing the CRISPR-Cas and CRISPR-Cpf1 systems to render the virulence factors of various bacteria ineffective. CRISPR (Clustered Regularly Interspaced Short Palindromic Repeats) is a prokaryotic adaptive defense system that provides resistance against alien replicons such as viruses and plasmids. CRISPRs evolved in bacteria as an adaptive immune system to defend against viral attack. Upon exposure to a virus, short segments of viral DNA are integrated into the CRISPR locus. RNA is transcribed from a portion of the CRISPR locus that includes the viral sequence. In certain preferred embodiments, rather than using CRISPR-Cas, one employs the CRISPR-associated endonuclease Cpf1. e.g. a CRISPR from *Prevotella* and *Francisella* 1 (Cpf1) nuclease for CRISPR-based genome editing, and incorporating 20150252358 to Maeder by this reference).

CRISPR-Cpf1 is a class II CRISPR effector that is distinct from Cas9, and is a single RNA-guided endonuclease that uses T-rich PAMs and generates staggered DNA double stranded breaks instead of blunt ends. Its smaller protein size and single RNA guide requirement makes CRISPR applications simpler and with more precise control. The human gut is a rich habitat populated by numerous microorganisms, each having a CRISPR system. To comply with written description and enablement requirements, incorporated herein by the following references are the following patent publications: 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 2015/0132263 to Liu; and 2014/0068797 to Doudna; 2014/0255351 to Berstad et al.; 2015/0086581 to Li; 2016/0311913 to Sun; PCT/US2014/036849 and WO 2013/026000 to Bryan; 2018/0127490 and 2018/0111984 to Bigal, et al.; 2018/0092899 to Liu, et al.; 2017/0240625 to Zeller, et al.; 2017/0342141 to Russo, et al.; 2018/0134772 to Sharma et al.; 2017/0201455 to Soares, et al.; 2017/0348303 to Bosse, et al.; 2017/0298115 to Loomis, et al.; and 2012/0294822 to Russo, et. al. 2018/0016647 and 2018/0016647 to Van Sinderen, et al.; 2018/0100169 to Soucaille, et al.; 2017/0232043 to Falb et al. and 2015/0045546 to Siksnys et al.

In various aspects of the present invention, CRISPR is employed to modify aspects for both bacterial and helminthes gene expression such that undesired normally transcribed proteins are excised or precluded from being expressed, thus precluding the deleterious effects of such proteins. Thus, normally dangerous species of bacteria and helminthes (from a perspective of such bacteria or helminthes causing disease in a human) can be modified so that such undesired effects of bacterial and helminthes infection are disrupted or deleted or lessened in a fashion that still permits the beneficial aspects of bacterial and helminthes proteins to be maintained.

Various embodiments of the present invention combine each of the above referenced four FLVR bacteria and using CRIPR, pathogenic and/or toxic elements are excised to preclude detrimental health issues that would normally be encountered using one or more of such bacteria, while preserving the immune system attributes attained by the presence of such bacteria. Preferably, the CRISPR modified bacteria of the FLVR species are then combined in a formulation suitable for use as either an oral composition (preferably administered via the strips as described herein). In certain embodiments, treatment of newborns so as to promote beneficial gut and oral microbiomes is achieved via strips or a vaginal cream (for the mother) such that a newborn is first exposed to such bacteria when traveling down the birth canal.

In certain embodiments of the present invention, antibiotic resistance of certain bacteria is modulated by employment of CRISPR to insert into the genome of a bacteria antibacterial sensitivity such that it can selectively be killed, if necessary, after it is employed to trigger desired immune responses in a new born or other individual. Thus, the various bacterial and helminthes species mentioned herein that are included in an or added to an Amish-soil may, in certain embodiments, be extracted and modified using CRISPR methods to do one of several things, including adding antibiotic sensitivity to various species so that they can be employed for triggering immune responses of an individual, and then later killed or rendered ineffective by the use of targeted antibiotics or anti-helminthes drugs.

In particular embodiments, directed to a topical composition of a bacterial and/or helminthes containing composition, such composition includes cells that have been transformed by use of CRISPR to delete particular undesired attributes of wild-type species, including the expression of disease causing proteins. Thus, creams, ointments, etc. may be employed as a vaginal pre-birth composition so that a new born, traveling down the vaginal canal, is exposed to a plurality of beneficial bacteria and/or helminthes proteins and other constituents such that a new born innate immune response is triggered to protect the new born from developing the variety of allergic and autoimmune diseases as described herein. In still other embodiments, a suitable oral or mucosal agent is administered to an individual's microbiome to provide a way to alter the existing microbiome of the individual such that migraines and cluster headaches can be prevented.

The use of CRISPR to tailor bacterial and helminthes components to either add desired characteristics and/or to delete known deleterious aspects of such bacteria or helminthes, provides a novel system and method for treating a variety of diseases such that bacteria and helminthes that would normally be considered too dangerous to employ as an agent to treat allergic, autoimmune conditions, migraines, cluster headaches, etc. is now rendered available for such purposes.

In various embodiments, DNA is injected into bacteria to restore antibiotic sensitivity to drug-resistant bacteria, and to also prevent the transfer of genes that create that resistance among bacteria. The CRISPR-CAS system may also be employed to render certain bacteria sensitized to certain antibiotics such that specific chemical agents can selectively choose those bacteria more susceptible to antibiotics, see, e.g. US Pat. Publication No. 2013/0315869 to Qimron, which is incorporated in its entirety by this reference.

The microbiome of an individual is disrupted by antibiotics and thus, the employment of CRISPR as a way to bypass common modes of multidrug resistance, while being selective for individual strains, is employed in various embodiments of the present invention to attain the benefits derived by the presence of particular bacteria and helminthes, including the triggering of desired immune development by newborns and other individuals, (e.g. those with multiple sclerosis, etc.) as well as in addressing the treatment and avoidance of migraines and cluster headaches. CRISPR-Cas systems employ CRISPR RNAs to recognize and destroy complementary nucleic acids. In various embodiments of the present invention, CRISPR-Cas systems are used as programmable antimicrobials to selectively kill bacterial species and strains such that desired selected targets can be focused on such that virtually any genomic location may be a distinct target for CRISPR-based antimicrobials, and that, in conjunction with an appropriate delivery vehicle, such as those employed by Bikard et al. and Citorik et al., one is able to effectively deploy a CRISPR-Cas system as an antimicrobial agent.

Another aspect of certain embodiments includes making synthetic CRISPR-containing RNAs that target genes of interest and using them with Cas enzymes. The specificity of CRISPR-Cas systems permits one to design methods to target a single bacterial species so that only essential genes from that one species is targeted and cut up. CRISPR-Cas systems are employed in various ways in the many embodiments of the present invention to retain the beneficial bacterial communities intact and to offer protection against undesired bacterial pathogens.

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is ~100 nt long.

The CRISPR system may be employed in various embodiments to strengthen antibiotics or to kill the bacteria altogether. By removing the bacteria's genes that make them antibiotic-resistant, CRISPR can boost the effectiveness of existing drugs. CRISPR can also be used to remove a bacteria's genes that make them deadly and facilitate RNA-guided site-specific DNA cleavage. Analogous to the search function in modem word processors, Cas9 can be guided to specific locations within complex genomes by a short RNA search string.

In certain embodiments, various particular bacterial species are focused on to delete or modulate their gene expressions, such species including the following: *Streptococcus; Escherichia coli, Streptococcus pyogenes*, and *Staphylococcus epidermidis*. This prokaryotic viral defense system has become one of the most powerful and versatile platforms for engineering biology.

In various embodiments, the CRISPR-Cas systems is employed to control the composition of the gut flora or oral microbiome, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas systems. Because of the sequence specificity of targeting, CRISPR-Cas systems may be used to distinguish strains separated by only a few base pairs. The specificity of targeting with CRISPR RNAs may be employed to readily distinguish between highly similar strains in pure or mixed cultures. Thus, in certain embodiments, varying the collection of delivered CRISPR RNAs is employed to quantitatively control the relative number of individual strains within a mixed culture in a manner to circumvent multidrug resistance and to differentiate between pathogenic and beneficial microorganisms.

In certain other aspects, particular embodiments of the present invention are directed to the use of CRISPR to excise certain prior infectious adenovirus DNA sequences that are considered responsible for the increased obesity of individuals harboring the same. Reference is made to Kovarik, U.S. Pat. No. 8,585,588, "Method and system for preventing virus-related obesity and obesity related diseases." After determining whether one has been infected with a particular virus, the viral DNA can then be excised via CRISPR-Cas to remove the previously inserted DNA, thus effectively reducing if not eliminating the adenovirus gene from the individual. Thereafter, to avoid being infected with such adenovirus again, practice of the method as set forth in U.S. Pat. No. 8,585,588 will lessen, if not prevent, reacquisition of such virus.

Controlling the composition of microbial populations is important in the context of desiring to expose individuals to particular species of bacterial and other microbes, helminthes, etc. and especially those that have not been previously exposed to antibiotics, antimicrobial peptides, and lytic bacteriophages. Use of CRISPR-Cas provides a generalized and programmable strategy that can distinguish between closely related microorganisms and allows for fine control over the composition of a microbial population for use in the present invention. Thus, the RNA directed immune systems in bacteria and archaea called CRISPR-Cas systems is employed in various embodiments of the present invention to selectively and quantitatively remove and/or alter individual bacterial strains based on sequence information to enable the fine tuning of exposure of desired antigens. Thus, such genome targeting using CRISPR-Cas systems allows one to specifically remove and/or alter individual microbial species and strains in desired ways.

In various embodiments, it is desirable to remove—using CRISPR-Cas systems—particular viable genes in pathogenic bacteria and/or other pathogenic portions (e.g plasmids, etc. of such bacteria) —while sparing other desired commensal bacteria, in order to provide exposure to desired immune developing proteins.

In various embodiments, one of skill in the art will appreciate that removal or alteration of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

Because preferred embodiments relate to the modification of microbes—rather than to the human genome—and especially only those microbes that show tropism for humans, the unintended consequences of employing Crispr-Cas on organisms is lessened, if not eliminated. Moreover, use of CRISPR-Cas to also insert genes that have controllable elements such that the cells are killed by triggering the expression of such genes, is another way to reduce if not eliminate concerns about an unintended release of a modified organism. These types of controls are well known to those of skill in the art and have been long employed, for example, by those involved in creating genetically engineered organisms, such as by inserting genes so that organisms become susceptible to various conditions, such as temperature, antibiotic exposure, etc., such that microbes that may somehow escape desired conditions will not be viable. Particular embodiments of the present invention are directed to the employment of four specific bacterial genera—*Lachnospira, Veillonella, Faecalibacterium* and *Rothia*. Modifying the human genome, made possible by the CRIPSR technique, has its own wonderful upsides and equally daunting downsides. Permanent deletion of genes from the human genome is much more controversial than deletion of bacterial genes. Thus, one desirable aspect of the present invention is directed to the far less controversial modification of gut microbes resident in the human being to promote health and to trigger the desired immune responses as described herein.

*Faecalibacterium prausnitzii*, which represent more than 5% of the bacteria in the intestine, is encouraged to populate the guts of patients. Such enhanced growth of this bacterium may also be employed to combat certain forms of inflammatory bowel disease. In various embodiments of the present invention, *Enterococcus faecalis* is are subjected to CRISPR-Cas procedures to remove undesired virulence and pathogenicity factors, such as several genes isolated from resistant enterococci (agg, gelE, ace, cylLLS, esp, cpd, fsrB) which encode virulence factors such as the production of gelatinase and hemolysin, adherence to caco-2 and hep-2 cells, and capacity for biofilm formation. Deletion and removal of certain antibiotic resistance, for example the acquisition of vancomycin resistance by enterococci, is desired also so as to properly and safely employ this bacteria in the present invention. In a particular embodiment, the addition of *E. faecalis* LAB3 1 is employed to trigger desired immune system responses.

CRISPR-Cas can be used on the various identified microbiome constituents to modify gene expression, including cutting of a gene, repress or activate a gene, etc. It can be employed to deliver desired regulators or any protein to a desired place on a genome of a microbe, thus permitting one to tailor the attributes of the microbiome of an individual to promote the health thereof, including the programmed triggering of particular immune responses in an infant. Because CRISPR-Cas acts before transcription occurs, it is able to be employed to target regulatory and other elements on the DNA of microbes that make up the microbiome. In certain embodiments, CRISPR-Cas is employed to deliver fluorescent markers to certain DNA sequences, thus permitting one to determine whether any particular sample has been treated in accordance with the present invention, thus ensuring, for example, identity of various materials, safety issues, types of enhanced soils, etc. This permits labeling of living cells with a desired color.

Many embodiments rely upon the ability to deliver agents via mucosal adhesive strips, such as described, for example, in U.S. Pat. No. 8,701,671, which is fully incorporated herein by this reference. In such a manner, one objective is to accept the beneficial traits of the microbiome's interaction with the human immune system while avoiding the infectious aspects of bacterial, viral and helminth aspects of such exposure to a human being. Thus, in various embodiments of the present invention, the engineering of communal bacteria with improved properties using a CRISPR/Cas system is employed. Thus, in certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene.

There exist various concerns about how CRISPR-Cas systems and method will be employed with respect to attempting to improve human health through and using a technology that cuts sections of DNA out of a genome, effecting permanent changes to the human DNA. Indeed, many in the scientific community are considering whether a moratorium on the use of this powerful and yet simple technology should be implemented until such time as all the risks involved can be better assessed. In the context of the present invention, however, this particular issue is either absent or of lesser importance due to one focus of many embodiments being relegated to the modification of DNA of the microbe genomes, rather than the human genome. Thus, the present invention is one way in which the human health concerns can be benefited directly by the use of a DNA deletion system without affecting the long term and permanent deletion of human genes. It is not believed to be obvious, let alone intuitive, that human health can be benefited by such a DNA deletion system used in a fashion that affects only gut microbes in a human's system. Moreover, the use of such a DNA modification system for microbes, but not for the direct deletion of genes from a human, and the use of such a system prior to the exposure of a human to such modified microbes, has not previously been done, especially with the added step of modifying select microbes having immune beneficial attributes—and especially using modified microbes that one would otherwise have considered to be pathogenic.

Individuals who have regular contact with livestock, such as farmers and their wives, have bacterial communities dominated by *Prevotella*, a type of bacteria that is also abundant in the gut microbiota of cattle and sheep. *Prevotella* are among the most numerous microbes culturable from the rumen and hind gut of cattle and sheep. Percentages vary but *Prevotella* is often the most common bacterial genus in the cattle. While certain aspects of particular embodiments are directed to the *Prevotella* genus, others are more focused on particular species within such genus, namely *P. intermedia*. The present inventors contend that the contributions of microbes to multiple aspects of human physiology and neurobiology in health and disease have up until now not been fully appreciated.

*Treponema denticola* is an oral anaerobic spirochete closely associated with the pathogenesis of periodontal disease—and the present inventors believe it is associated with numerous systemic diseases, including Alzheimer's disease. The *T. denticola* major surface protein (MSP), involved in adhesion and cytotoxicity, and the dentilisin serine protease are key virulence factors of this organism. Thus, one aspect of the present invention relates to the use of CRISPR-Cas or Cpf1 to target these virulence factors and thus, excise them from *T. denticola* so as to render it susceptible to antibiotics so as to reduce its presence in the oral microbiome, thus advancing the prevention of not only migraines, cluster headaches and dizziness, but for Alzheimer's disease as well. Periodontal diseases are polybacterially induced, multifactorial inflammatory processes of the tooth attachment apparatus and are the primary cause of tooth loss after the age of 35. The ability of such disease to escape detection and the failure of many to regularly visit a dentist to diagnose such a disease, leads to the prevalence of Alzheimer's disease as we see today. The elderly often show neglect of oral hygiene which can stimulate recurrent chronic oral infection, which promotes inflammation and then leads to confusion and dementia. Interfering with inflammation is thus one objective of the present invention and in certain embodiments, it is beneficial to combine anti-inflammatory agents with antibacterials.

The periodontopathogenic spirochete *T. denticola* possesses a number of virulence factors including motility, the ability to attach to host tissues, coaggregation with other oral bacteria, complement evasion mechanisms, and the presence of several outer sheath and periplasmic proteolytic and peptidolytic activities. Two components associated with the spirochetes' outer sheaths and extracellular vesicles are the major surface protein (also known as the major outer sheath protein [MSP]) and a serine protease, dentilisin, previously known as the chymotrypsin-like protease. Recent bioinformatics analysis reclassified dentilisin as a member of the subtilisin rather than the chymotrypsin family. Dentilisin is involved in the degradation of membrane basement proteins (laminin, fibronectin, and collagen IV), serum proteins (fibrinogen, transferrin, IgG, and IgA), including protease inhibitors ($\alpha$1-antitrypsin, antichymotrypsin, antithrombin, and antiplasmin), and bioactive peptides. Degradation of tight junction proteins by dentilisin seems to enable the penetration of epithelial cell layers by this oral spirochete. MSP is a major antigen with pore-forming activity. This abundant membrane protein mediates the binding of *T. denticola* to fibronectin, fibrinogen, laminin, and collagen, induces macrophage tolerance to further activation with lipopolysaccharide (LPS), and elicits cytotoxic effects in different cell types.

One object of the present invention is to employ LL-37 against *T. denticola*, especially employing the strips as set forth herein. Saliva inhibits dentilisin, attenuating its virulence properties but conserving LL-37 activity. Thus one aspect of the present invention is directed to the use of LL-37 to kill *T. denticola*. The human host defense peptide LL-37 is preferably administered via the strips of the present invention, especially those having encapsulated pockets of the agent such that administration thereof can be achieved by the patient upon tongue pressure being applied to a frangible shell present as part of the strip. Deficiency in the human host defense peptide LL-37 has previously been correlated with severe periodontal disease. *Treponema denticola* is an oral anaerobic spirochete closely associated with the pathogenesis of periodontal disease. *Treponema denticola* is an important periodontal pathogen capable of tissue invasion. Its chymotrypsin-like proteinase (CTLP) can degrade a number of basement membrane components in vitro, thus suggesting a contribution to tissue invasion by the spirochete. Periopathogen survival is dependent upon evasion of complement-mediated destruction. *Treponema denticola*, an important contributor to periodontitis, evades killing by the alternative complement cascade by binding factor H (FH) to its surface.

In the healthy subgingival crevice, *Treponema denticola* account for ~1% of the total bacteria. With the progression of periodontitis, the abundance of oral treponemes increases dramatically and can reach 40% of the total bacterial population. Disease severity correlates specifically with the outgrowth of *Treponema denticola* and other bacterial species of the red microbial complex.

*Treponema denticolais* is an oral spirochete and periopathogen that transitions from low abundance in healthy subgingival crevices to high abundance in periodontal pockets. The *T. denticola* response regulator AtcR harbors the relatively rare, LytTR DNA binding domain. LytTR domain containing response regulators control critical transcriptional responses required for environmental adaptation. The functional diversity of the proteins encoded by the putative AtcR regulon suggests that AtcR sits at the top of a regulatory cascade that plays a central role in facilitating *T. denticola*'s ability to adapt to changing environmental conditions and thrive in periodontal pockets.

While most bacteria, including spirochetes, employ two component regulatory (TCR) systems and cyclic nucleotides to regulate adaptive responses, certain embodiments of the present invention are directed to the *T. denticola* genetic regulatory system and signaling mechanisms to decrease the growth and maintenance thereof in the oral cavity.

One general take-away from the present invention relates to how best to adopt practices that establish and retain and maintain oral health such that individuals do not suffer from the array of different maladies that are now understood to be related, whether directly or indirectly, to oral health. For example, it is common for individuals to get their teeth cleaned a few times a year. Upon such a cleaning procedure, however, the dental surfaces are relatively "clean" of the biofilms that where established thereon since the last dental cleaning visit. Instead of proactively applying a beneficial composition of beneficial bacteria to the cleaned surfaces, however, it is common and typical practice to simply have the dental patient leave the dental office, after scheduling another 6 month visit, and thus leave the colonization of the dental surfaces up to the chance presence of bacteria that may then be present in the person's mouth or surrounding environments. Given the growing and recent knowledge of the nature of oral biofilms, populated by a myriad of bacteria of different but coexisting species of bacteria, it is one aspect of the present invention to purposefully contact a person's recently cleaned teeth with a composition that contains bacteria believed to be especially beneficial to the establishment of a "healthy" biofilm. This entails, in certain embodiments, a progressive and successive contact of a person's teeth with different bacteria, with the staging of contact with various bacteria based upon the known synergistic relationship between oral bacteria, and with the emphasis being to limit the most pathogenic bacteria known to cause some of the prevalent problems suffered by humans.

The limitation of the growth and establishment of a certain spirochete, namely, *Treponema denticola*, is a focus of various embodiments. The use of CRISPR-Cas and similar technologies to alter the genetic makeup of such spirochete so as to lessen its infectivity in various regards is yet another way to accomplish this objective. Excision or retardation of the various virulence factors for this bacteria are other ways in which such a goal can be achieved. Still other ways to accomplish this objective involves interfering with the admittedly complex interactions and associations of other bacteria responsible for the growth of spirochetes in the oral cavity. Thus, by directly addressing still other supporting bacteria, one is able to indirectly, but nonetheless effectively, limit the progression of spirochetes, and in particular, *Treponema denticola*, establishment and growth. By doing so, one is saved from the ravages of Alzheimer's disease, as well as the several other diseases that are noted as being related to the oral health of a person. Providing a tooth contacting substance at the time of a dental cleaning is preferred, as well as possible re-applications of compositions by the individual so as to establish a preferred buildup of a beneficial biofilm having particular bacteria constituents. Such formulations for beneficial oral cavity health may vary dependent upon many factors, such as the particular diet of the individual, the race of the individual, the age, etc. It is known that bacterial populations vary greatly between individuals, as well as within the same individual based on health and age. Thus, selection of particular compositions having a pre-determined composition of bacteria formats and variety are contemplated by the present invention.

Bacterial species are able to use various energy sources, including light and diverse organic and inorganic chemicals, for growth and metabolism. These energy sources are used to produce an electrochemical gradient that provides an electron donor for metabolism and allows maintenance of a membrane potential and proton motive force. The energetics of living systems are driven by electron transfer processes in which electrons are transferred from a substrate, which is thereby oxidized, to a final electron acceptor, which is thereby reduced. In certain embodiments, it is possible to control metabolism by linking biochemical processes to an external electrochemical system, with such linking of biochemical and electrochemical systems permitting the use of electricity as a source of electrons for biotransformation reactions. A reversible biochemical-electrochemical link allows for conversion of microbial metabolic and/or enzyme catalytic energy into electricity.

In still other embodiments, employment of technology described in U.S. Pat. No. 9,131,884 to Holmes is employed to achieve desired further steps to address communication of biological disease status to a third party. For example, in certain embodiments, a medical device is associated with a mucosal strip that comprises a microarray having a bioactive agent capable of interacting with a disease marker biological analyte and a reservoir having at least one therapeutic agent, with the device able to release the therapeutic agent(s) from the medical device. In certain embodiments, at least two microchips with a microarray scanning device adapted to obtain physical parameter data of an interaction between the disease marker biological analyte and the bioactive agent is employed. A biometric recognition device is configured to compare the physical parameter data with an analyte interaction profile. The therapeutic agent releasing device controls the release of the therapeutic agent from the reservoir. The interface device facilitates communications between the microarray scanning device, biometric recognition device and the therapeutic agent releasing device. An energy source to power the medical device can take several forms, including biologically activated batteries that are preferably associated with the strip.

In certain other embodiments, sugar is used as a source of energy, notably glucose that is converted into different sugars via an enzymatic cascade to provide necessary energy to create an electrochemical gradient. This, in turn, is used to power an enzyme that synthesizes adenosine triphosphate (ATP). In contrast to natural catabolic pathways for cellular glucose oxidation, a preferred embodiment does not rely on ATP as an energy carrier. Instead, two redox enzymes oxidize glucose, generating reduced nicotinamide adenine dinucleotide (NADH) as the sugar is broken down. Another series of enzymes (as many as ten additional enzymes) further breakdown the sugars and feed them back to the redox enzymes to produce more NADH, with water and carbon dioxide being the only by-products. NADH is a reducing agent and acts as an electron shuttle that carries electrons in living cells from one molecule to another. NADH first transfers the electrons stripped from the glucose to a mediator with the help of an enzyme. The mediator then delivers these electrons to the battery's electrode, rendering it available to power an electronic device. Such a battery mimics the way a living cell transfers electrons from one molecule to another to generate power, it runs on renewable sugars, and has a high-energy storage density, rechargeable providing an additional sugar solution. Malodextrin—a polymer made up of glucose subunits—may be employed together with particular different enzymes able to strip electrons from a single glucose molecule, thus harnessing the generated energy to power an electrical device.

To comply with written description and enablement requirements, incorporated herein by the following references are the following patent publications: 2015/0216917 to Jones; 2015/0361436 to Hitchcock; 2015/0353901 to Liu; 9,131,884 to Holmes; 2015/0064138 to Lu; 2015/0093473 to Barrangou; 2012/0027786 to Gupta; 2015/0166641 to Goodman; 2015/0352023 to Berg.

While specific embodiments and applications of the present invention have been described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other methods and systems for carrying out the several purposes of the present invention to instruct and encourage the prevention and treatment of various human diseases. It is important, therefore, that the claims be regarded as including any such equivalent construction insofar as they do not depart from the spirit and scope of the present invention.

What is claimed is:

1. A method to facilitate the growth of desired bacteria in a human's mouth to limit the number of pathogenic bacteria, to maintain oral health and to establish a biofilm in a human subject's mouth, comprising,
    after a human subject has cleaned their teeth, killing gram negative bacteria that are associated with periodontitis;
    providing to the human subject a bacterial composition comprising beneficial bacteria adapted to form a biofilm, said beneficial bacteria comprising a bacterium of the genus *Rothia*, and wherein said bacterial composition does not inhibit growth of a bacterium of species *Lactobacillus salivarius*, and wherein said step of killing comprises using a clustered regularly interspaced short palindromic repeats (CRISPR)-CRISPR associated protein (Cas) system or a CRISPR from *Prevotella* and *Francisella* 1 (Cpf1) system.

2. The method as set forth in claim 1, wherein said beneficial bacteria is provided on an oral strip.

3. The method as set forth in claim 1, wherein said strip has a first side and a second side, said second side having a bioadhesive that is adapted to bind to a mucosal membrane of the human subject for at least 1 hour while inside the human subject's mouth.

4. The method as set forth in claim 1, wherein said beneficial bacteria further comprises *Lactobacillus reuteri* in an amount sufficient to induce oxytocin production.

5. The method as set forth in claim 1, wherein said gram negative bacteria comprises *Treponema denticola*.

6. The method as set forth in claim 1, wherein the bacterial composition is administered orally.

7. The method as set forth in claim 1, wherein the bacterial composition does not inhibit growth of a second bacterium selected from at least one of the species *Streptococcus mutans* and *Lactobacillus fermentum*.

8. The method of claim 1, wherein the step of administering comprises providing a buccal bioadhesive strip having a first side and a second side, the second side having a bioadhesive that is adapted to bind to a mucosal membrane for at least 1 hour while inside the human subject's mouth, wherein said strip includes at least one encapsulated feature containing said bacterial composition.

9. The method as set forth in claim 1, wherein the bacterial composition does not inhibit growth of a bacterium of species *Lactobacillus fermentum*.

10. The method as set forth in claim 1, wherein the method further comprises administering a prebiotic to the human.

11. The method as set forth in claim 1, further comprising reducing the population of bacteria that spirochetes depend upon to thrive and grow.

12. The method as set forth in claim 1, wherein said bacteria comprise *P. gingivalis*.

13. The method as set forth in claim 1, further comprising limiting the population of *Treponema denticola*.

14. A method to facilitate the growth of desired bacteria in a human's mouth to limit the number of pathogenic bacteria, to maintain oral health and to establish a biofilm in a human subject's mouth, comprising,
    after a human subject has cleaned their teeth, killing gram negative bacteria that are associated with periodontitis;
    providing to the human subject a bacterial composition comprising beneficial bacteria adapted to form a biofilm, said beneficial bacteria comprising a bacterium of the genus *Rothia*, and wherein said bacterial composition does not inhibit growth of a bacterium of species) *Lactobacillus salivarius*, and reducing the population of bacteria that spirochetes depend upon to thrive and grow using a clustered regularly interspaced short palindromic repeats (CRISPR)-CRISPR associated protein (Cas) system or a CRISPR from *Prevotella* and *Francisella* 1 (Cpf1) system.

15. The method as set forth in claim 14, wherein said beneficial bacteria is provided on an oral strip.

16. The method as set forth in claim 14, wherein said strip has a first side and a second side, said second side having a bioadhesive that is adapted to bind to a mucosal membrane of the human subject for at least 1 hour while inside the human subject's mouth.

17. The method as set forth in claim 14, wherein said beneficial bacteria further comprises *Lactobacillus reuteri* in an amount sufficient to induce oxytocin production.

18. The method as set forth in claim 14, wherein said gram negative bacteria comprises *Treponema denticola*.

19. The method as set forth in claim 14, wherein the bacterial composition does not inhibit growth of a second bacterium selected from at least one of the species *Streptococcus mutans* and *Lactobacillus fermentum*.

20. The method as set forth in claim 14, wherein the bacterial composition does not inhibit growth of a bacterium of species *Lactobacillus salivarius*.

\* \* \* \* \*